US007674809B2

(12) United States Patent
Makovec et al.

(10) Patent No.: US 7,674,809 B2
(45) Date of Patent: Mar. 9, 2010

(54) ANTI-INFLAMMATORY AND ANALGESIC HETEROCYCLIC AMIDINES THAT INHIBIT NITROGEN OXIDE (NO) PRODUCTION

(75) Inventors: Francesco Makovec, Lesmo (IT); Antonio Giordani, Pavia (IT); Roberto Artusi, Rho (IT); Stefano Mandelli, Cambiago (IT); Ilario Verpilio, Pregnana Milanese (IT); Simona Zanzola, Milan (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 1146 days.

(21) Appl. No.: 11/068,347

(22) Filed: Mar. 1, 2005

(65) Prior Publication Data

US 2005/0197331 A1 Sep. 8, 2005

(30) Foreign Application Priority Data

Mar. 1, 2004 (IT) .......................... TO2004A0125

(51) Int. Cl.
  *A61K 31/425* (2006.01)
  *A61P 29/02* (2006.01)
  *C07D 277/64* (2006.01)
  *C07D 277/66* (2006.01)
  *C07D 285/14* (2006.01)
  *A61K 31/517* (2006.01)
  *C07D 239/94* (2006.01)
(52) U.S. Cl. .................. 514/367; 548/159; 548/178
(58) Field of Classification Search ................. 514/367; 548/159, 178
See application file for complete search history.

(56) References Cited

U.S. PATENT DOCUMENTS

| 6,613,787 B2 * | 9/2003 | Wilson et al. ............... 514/394 |
| 2004/0053981 A1 * | 3/2004 | Wilson et al. ............... 514/367 |
| 2005/0209291 A1 * | 9/2005 | Ramnauth et al. ........... 514/367 |

FOREIGN PATENT DOCUMENTS

| JP | 10 265 450 | 10/1998 |
| WO | WO 96/19440 A1 | 6/1996 |
| WO | WO 96/24588 A1 | 8/1996 |
| WO | WO 2004/014885 A1 | 2/2004 |

OTHER PUBLICATIONS

Wayland E. Noland, et al.: "Nitration of Indoles. IV" The Nitration of 2-Phenylindole, vol. 31, pp. 65-69, Jan. 1996.
C. M. Orlando, Jr., et al.: "Methyl Aryl Ether Cleavage in Benzazole Syntheses in Polyphosphoric Acid", J. Org. Chem., vol. 35, No. 9, 1970, pp. 3147-3149.
Alejandro Alvarez, et al: "Synthesis of 3-Arylpyrroles and 3-Pyrrolyacetylenes by Palladium-Catalyzed Coupling Reactions", J. Org. Chem., vol. 57, No. 6, 1992, pp. 1653-1656.
Mercedes Amat, et al: "Palladium(0)-Catalyzed Heteroarylation of 2- and 3-Indolyzine Deriatives. An Efficient General Method for the Preparation of (2-Pyridyl)indoles and Their Application to Indole Alkaloid Synthesis", J. Org. Chem., vol. 62, No. 10, 1997, pp. 3158-3175.
Laura C. Green, et al: "Analysis of Nitrate, Nitrite, and [$^{15}$N]Nitrate in Biological Fluids", Analytical Biochemistry, vol. 126, 1982, pp. 131-138.
Kenneth J. Armour, et al: "Activation of the Inducible Nitric Oxide Synthase Pathway Contributes to Inflammation-Induced Osteoporosis by Suppressing Bone Formation and Causing Osteoblast Apoptosis", Arthritis & Rheumatism, vol. 44, No. 12, Dec. 2001, pp. 2790-2796.
F.D. Bellamy, et al: "Selective Reduction of Aromatic Nitro Compounds With Stannous Chloride In Non Acidic and Non Aqueous Medium", Tetrahedron Letters, vol. 25, No. 8, 1984, pp. 839-842.
Enzo Cereda, et al: "Synthesis and Biological Evaluation of New Antimuscarinic Compounds with Amidine Basic Centers. A Useful Bioisoteric Replacement of Classical Cationic Heads", J. Med. Chem., vol. 33, No. 8, 1990, pp. 2108-2113.
Jon L. Collins, et al: "N-Phenylamidines as Selective Inhibitors of Human Neuronal Nitric Oxide Synthase: Structure-Activity Studies and Demonstration of in Vivo Activity", J. Med. Chem, vol. 41, No. 15, pp. 2858-2871.

(Continued)

*Primary Examiner*—James O Wilson
*Assistant Examiner*—Tamthom N Truong
(74) *Attorney, Agent, or Firm*—Sughrue Mion, PLLC

(57) ABSTRACT

Heterocyclic amidines with anti-inflammatory and analgesic activity that inhibit nitrogen oxide production, of formula (I):

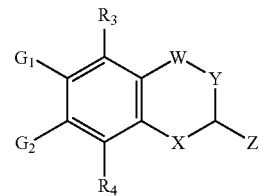

in which:
  $G_1$ and $G_2$ are hydrogen, halogen, hydroxyl, $C_1$-$C_4$ alkoxy, $C_1$-$C_4$ alkyl, and an amidino substituent of formula Q, provided that, for each compound of formula (I), only one of the two substituents $G_1$ or $G_2$ is an amidino substituent of formula Q:

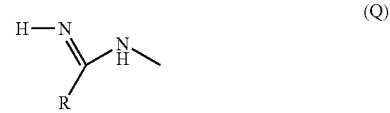

and in which the substituents W, Y and X are combined to form 9- or 10-membered bicyclic heteroaromatic derivatives containing up to 2 hetero atoms in the same ring; and
  Z is an aryl or heteroaryl group, a linear or branched $C_1$-$C_6$ alkyl or alkenyl chain, a $C_1$-$C_4$ alkyl-aryl group or a $C_1$-$C_4$ alkyl-heteroaryl group.

8 Claims, No Drawings

OTHER PUBLICATIONS

B. Dugas, et al: "Nitric Oxide, a vital poison inside the immune and inflammatory network", 63rd Forum in Immunology, www.bl.uk, pp. 664-670, (Res. Immun.) 1995, vol. 146, No. 9.

J. Eustache, et al: "N, N'-Bis(benzylooxycarbonyl)acetamidine, a Versatile Reagent for the Conversion of Amines and Alcohols to Acetamidines", Tetrahedron Letters, vol. 36, No. 12, 1995, pp. 2045-2046.

Barnett S. Pitzele, "The inhibition of isoforms of nitric oxide synthase: non-cardiovascular aspects", Expert Opinion on Therapeutic Patents, vol. 9, No. 5, 1999, pp. 549-556.

Julieta Gentiletti, et al: "Does Vascular Endothelial Growth Factor Play a Role in Interleukin-6 Receptor Antagonist Therapy for Rheumatoid Arthritis", Arthritis & Rheumatism, vol. 48, No. 6, Jun. 2003, pp. 1471-1474.

Johnathan G. Grieb, et al: "Synthesis of 2-Aryl-1-(Phenylsulfonyl)Pyrroles", Synthetic Communications, vol. 25, No. 14, 1995, pp. 2145-2153.

Philippe Gros, et al: "Efficient and Regioselective Access to Bis-heterocycles via Palladium-Catalysed Coupling of Organostannanes and Organozincates Derived from C-6 Lithiated 2-Methoxypyridine", Synthesis, No. 5, ISSN 0039-7881, 1999, pp. 754-756.

Jwanro Hassan, et al: "Aryl-Aryl Bond Formation One Century after the Discovery of the Ullmann Reaction", Chem. Rev., vol. 102, No. 5, 2002, 1359-1469.

Ying-Hung So, et al: "Mechanism of Polyphosphoric Acid and Phosphorus Pentoxide-Methanesulfonic Acid as a Synthetic Reagents for Benzoxazole Formation", J. Org. Chem., vol. 62, No. 11, 1997, pp. 3552-3561.

Adrian J. Hobbs, et al: "Inhibition of Nitric Oxide Synthase as a Potential Therapeutic Target", Annu. Rev. Pharmacol. Toxicol., vol. 39, 1999, pp. 191-220.

Hiroaki Ito, et al: "Anti-IL-6 receptor monoclonal antibody inhibits leukocyte recruitment and promotes T-cell apoptosis in a murine model of Crohn's disease", Journal of Gastroenterology, vol. 37, Suppl XIV, 2002, pp. 56-61.

Peter Jutzi, et al: "Zur Synthese Einiger Neuer Heterocyclisch Substituierter Stannane", Journal of Organometallic Chemistry, vol. 246, 1983, pp. 163-168.

Elaine Kuo, et al: "Facile Reduction of Aromatic Nitro Compounds to Anilines with 2-Propanol and Raney Nickel", Synthetic Communications, vol. 15, No. 7, 1985, pp. 599-602.

Tuanli Yao, et al: "Synthesis of Isocoumarins and α-Pyrones via Electrophilic Cyclization", J. Org. Chem. Article, vol. 68, No. 15, 2003, pp. 5936-5942.

Jung Sun Kim, et al: "Structure-Activity Relationships of Benzimidazoles and Related Heterocycles as Topoismerase I Poisons", Bioorganic & Medicinal Chemistry, vol. 4, No. 4, 1996, pp. 621-630.

Dajie Li, et al: "Nitroarylstannanes as Synthons for the Preparation of Phenanthridine and Benzo[i]phenanthridine Derivatives", J. Org. Chem, vol. 65, No. 9, 2000, pp. 2802-2805.

Bert U.W. Mases, et al: "A New Approach Towards the Synthesis of 3-Amino-6-(hetero)arylpyridazines Based on Palladium Catalyzed Cross-Coupling Reactions", Tetrahedron, vol. 56, 2000, pp. 1777-1781.

Masanori Kosugi, et al: "Preparation of Aryltributyltin Having Electron-withdrawing Group by Palladium Catalyzed Reaction of Hexabutlditin with Aryl Iodide", Bull. Chem. Soc., vol. 56, 1983, pp. 3855-3856.

Rachid Baati, et al: "An Improved Method for the Preparation of Amidines via Thiophenylimidic Esters", Synthesis, ISSN 0039-7881, No. 6, 1999, pp. 927-929.

Salvador Moncada, et al: "The L-Arginine-Nitric Oxide Pathway", The New England Journal of Medicine, vol. 329:2002-2012, No. 27, Dec. 30, 1993, pp. 1-39.

Hideko Nakahara, et al: "Anti-Interleukin-6 Receptor Antibody Therapy Reduces Vascular Endothelial Growth Factor Production in Rheumatoid Arthritis", Arthritis & Rheumatism, vol. 48, No. 6, Jun. 2003, pp. 1521-1529.

Atsuko Nose, et al: "Selective Reduction of Aromatic Nitro Compounds with Nickel Boride", Chem. Pharm. Bull., vol. 37, No. 3, 1989, pp. 816-818.

Robert J. Perry, et al: "Synthesis of 2-Arylbenzoxazoles via the Palladium-Catalyzed Carbonylation and Condensation of Aromatic Halides and o-Aminophenols", J. Org. Chem., vol. 57, No. 10, 1992, 2883-2887.

Byoung Se Lee, et al: "A New Effective Synthesis of 6-Nitroquipazine", Heterocycles, vol. 48, No. 12, 1998, pp. 2637-2641.

Barry G. Shearer, et al.: "S-2-Napthylmethyl Thloacetimidate Hydrobromide: A New Odorless Reagent for the Mild Synthesis of Subsituted Acetamidines", Tetrahedron, vol. 38, No. 2, 1997, pp. 179-182.

Takao Sakamoto, et al: "Preparation of π-Deficient Heterarylzinc Halides by Oxidative Addition of Active Zinc and Its Palladium-Catalyzed Reaction", Tetrahedron, vol. 49, No. 43, 1993, pp. 9713-9720.

Tahir N. Majid, et al: "A New Preparation of Highly Functionalized Aromatic and Heteroaromatic Zinc and Copper Organometallics", Tetrahedron Letters, vol. 31, No. 31, 1990, pp. 4413-4416.

Stephanie L. Hargreaves, et al: "The Synthesis of Substituted Pyridylpyrimidine Fungicides Using Palladium-Catalysed Cross-Coupling Reactions", Tetrahedron Letters, vol. 41, 2000, pp. 1653-1656.

Toshifumi Tetsuka, et al: "Nitric Oxide Amplifies Interleukin 1-induced Cyclooxygenase-2 Expression in Rat Mesangial Cells", J. Clin. Invest., vol. 97, No. 9, May 1996, pp. 2051-2056.

Akihiko Tsuruoka, et al: "Synthesis and Antifungal Activity of Novel Thiazole-Containing Triazole Antifungals. II Optically Active ER-30346 and Its Derivatives", Chem. Pharm. Bull., vol. 46, No. 4, 1998, pp. 623-630.

Jean Jacques Vanden Eynde, et al: "A New Convenient Method for the Preparation of 2-Substituted Quinazolines", Synthesis, Sep. 1993, pp. 867-869.

Rob J. Van't Hof, et al: "Nitric Oxide and Bone", Immunology, vol. 103, 2001, pp. 255-261.

D. Neils Watkins, et al: "Regulation of the inducible cyclo-oxygenase pathway in human cultured airway epithelial (A549) cells by nitric oxide", British Journal of Pharmacology, vol. 121, 1997, pp. 1482-1488.

Michele A. Weidner-Wells, et al: "Amidino Benzimidazole Inhibitors of Bacterial Two-Component Systems", Bioorganic & Medicinal Chemistry Letters, vol. 11, 2001, pp. 1545-1548.

D.W. Hein, et al: "The Use of Polyphosphoric Acid in the Synthesis of 2-Aryl- and 2-Alkyl-substituted Benzimidazoles, Benzoxazoles and Benzothiazoles", Bounc Book Laboratories, vol. 79, Jan. 20, 1957, pp. 427-429.

Dale L Boger: "A Convenient Preparation of 2-Substituted Benzothiazoles[1]", Department of Chemistry, Harvard University, J. Org. Chem, vol. 43, No. 11, 1978, pp. 2296-2297.

Anna Arnoldi, et al.: "A Simple Synthesis of 2-Substituted I-Benzothiophenes and 3-Substituted 2H-1 Benzothiopyrans", Communications, Feb. 1988, pp. 155-157.

Glaxo Group Ltd.: W09962875, "Nitric Oxide Synthase Inhibitors" Export Opinion on Therapeutic Patents, vol. 10, No. 7, 2000, pp. 1143-1146.

* cited by examiner

ANTI-INFLAMMATORY AND ANALGESIC HETEROCYCLIC AMIDINES THAT INHIBIT NITROGEN OXIDE (NO) PRODUCTION

The subject of the present invention are novel heteroaromatic amidine derivatives with anti-inflammatory and analgesic activity, pharmaceutically acceptable salts thereof, methods for preparing the said derivatives and formulations thereof, and also their therapeutic use.

In particular, the present invention relates to the compounds of Formula (I) and to the corresponding pharmaceutically acceptable salts, which show marked anti-inflammatory and analgesic activity, both by inhibiting the production of nitrogen oxide (NO) and by inhibiting the production of prostaglandins, such as $PGE_2$, and of cytokines such as interleukin-6 (IL-6), and are therefore useful therapeutic agents in the treatment of pathologies associated with excessive production of NO due to expression of inducible NOS and of inflammatory prostaglandins produced by COX-2 and cytokines such as IL-6.

Among the typical pathologies associated with anomalous production of NO, prostaglandins and cytokines are: rheumatoid arthritis, osteoarthritis, synovitis, neuropathies, ulcerative colitis and Crohn's disease, and inflammatory or atherosclerotic pathologies of the cardiovascular system.

Nitrogen oxide (NO) is a chemical mediator that is widely involved in various physiological phenomena. At the start of the 1980s it was discovered that the factor with vasodilatory activity released by the endothelium (endothelium-derived relaxing factor, EDRF), which causes acetylcholine-mediated vasodilation, is not other than NO released by the cells of the vascular endothelium. This discovery was concomitant with the identification of the metabolic pathway mediated by the enzyme NO synthetase (NOS), which, starting with L-arginine, leads to L-citrulline and NO (Moncada S., Higgs A., N. Engl. J. Med., 1993, 329 (27), 2002-12).

Three isoforms of the enzyme NOS have been identified. The isoforms hitherto characterized are two constitutive isoforms, known as the type I or neuronal isoform (nNOS) and the type III or endothelial isoform (eNOS), and an inducible isoform, known as the type II or iNOS isoform.

iNOS is induced after activation, in particular cells, in response to an endotoxin- or cytokine-induced inflammatory stimulus; the control of iNOS is thus regulated at the level of synthesis of the protein, which, once expressed, produces high concentrations of NO for relatively long times.

Macrophages, endothelial cells, endothelial smooth muscle, chondrocytes, osteoblasts and the pulmonary epithelium are particularly effective as regards the expression of iNOS following an inflammatory stimulus.

A noteworthy difference between the constitutive enzymes and the inducible enzyme is thus a delayed but more sustained and longer-lasting production of NO mediated by the inducible enzyme, together at the site where this mediator is released. This determines the differences that give rise to the NO-mediated physiological or pathophysiological effects.

Thus, whereas NO released from the constitutive enzymes acts as a mediator within a signal translation system, for instance the activation of guanylate cyclase by the NO released from the endothelial cells, which, by raising the levels of cGMP, controls the vascular tonus and muscle relaxation.

On the other hand, NO released from the inducible isoform acts as a cytotoxic molecule, involved in body defence mechanisms (Dugas B. et al.; Res. Immunol. 1995, 146 (9) 664-70).

Thus, whereas, on the one hand, when appropriately regulated, iNOS is an enzyme of fundamental importance for the immune system, imbalances in the synthesis of iNOS-mediated NO may lead to a whole range of pathologies involved in inflammatory processes or involving the immune system as indicated previously.

It has been demonstrated that iNOS is induced in every species by inflammatory processes and that suppression of its activity is effective in reducing inflammatory symptomatologies (A. J. Hobbs et al., Annual Review of Pharmacology and Toxicology, 1999, 39, 191-220).

It is believed, on the one hand, that NO is involved, together with other mediators, in physiological processes of plasticity and reconstitution of bone tissue, whereas, on the other hand, the involvement of iNOS-derived NO in the inflammatory process and in the degeneration of the tissues characterized in rheumatoid arthritis (RA) and osteoarthritis (OA) has been shown (van't Hof R J, Ralston S H.; Nitric oxide and bone, Immunology, 2001 July; 103(3): 255-261).

In point of fact, iNOS has been found in the synovia and cartilage of patients suffering from rheumatoid arthritis (RA) and osteoarthritis (OA), and it has been demonstrated that both the synovial cells and the chondrocytes, in vitro, are capable of expressing iNOS by stimulation with cytokines. In addition, it has been shown that NO is a powerful stimulator of chondrocyte and synovial cell apoptosis, which would explain the tissue degeneration observed in RA (Armour K J, et al., Arthritis Rheum. 2001 December; 44(12):2790-6).

The high concentration of NO in patients with ulcerative colitis also suggests in this case an involvement of iNOS in this pathology.

With the identification of NO as the critical mediator of a congruous number of physiopathological processes, pharmacological control of its production is clearly of therapeutic potential. The first agents appearing in the literature capable of interfering with the production of NOS-mediated NO were enzyme inhibitors which were analogues of the substrate (L-arginine), among the following: L-NMMA ($N^G$-methyl-L-arginine), L-NNA ($N^G$-nitro-L-arginine), L-NAME ($N^G$-nitro-L-arginine methyl ester), L-NAA ($N^G$-amino-L-arginine) and L-NIO ($N^\delta$-iminoethyl-L-ornithine).

On account of their weak selectivity between the various isoforms, the clinical use of these inhibitors requires great care, since inhibition of the constitutive forms may have serious consequences, such as hypertension and more severe possible effects such as thrombosis and tissue damage. Thus, even though the therapeutic use of sparingly selective inhibitors is possible, the use of agents capable of selectively controlling the production of NO from iNOS is of greater therapeutic potential.

In the last decade, a large number of studies have appeared in the literature, documenting intense research in this direction (Exp. Opin. Ther. Patents, 1999, 9, 549-556; Exp. Opin. Ther. Patents, 2000, 10, 1143-1146); among these, NOS inhibitors of non-amino acid structure have been reported, which are for the majority based on bioisosteres of the guanidine group present in the structure of arginine, for instance S-alkylisothiourea, guanidine and amidine.

All these publications and studies reveal the therapeutic need for pharmacological agents based on modulation of the activity of iNOS characterized by a better pharmacological profile.

Prostaglandins (PGE) are inflammation mediators generated by the enzyme cyclooxygenase (COX). The inducible isoform (COX-2) is overproduced ("upregulated") in the inflamed tissues and this leads to an increased synthesis of PGE.

Interactions exist between NOS and COX systems, and the role of NO in inflammation may therefore depend not only on its direct effect but also on its modulatory effect on PGE biosynthesis.

Interleukin-6 (IL-6) is a cytokine whose overexpression is associated with the physiopathology of various human diseases, for instance Crohn's disease [see Ho et al., J. Gastroenterol. Suppl. 14, 56-61 (2002)] or rheumatoid arthritis [see Nakahara H. et al.; Arthritis Rheum. 48 (6), 1471-4 (2003)].

Since the enzymes iNOS and COX-2, just like the cytokine IL-6, the effect of which has been discussed above, are expressed in conjunction with inflammatory processes, demonstrating large effects in the establishment and development of the discussed pathologies, it would clearly be advantageous to be able to use a medicinal product capable of exhibiting inhibitory action on the iNOS-mediated production of NO and the formation of COX-2-mediated inflammatory prostaglandins, not to mention the expression of a cytokine, for instance IL-6.

The compounds of the present invention represented by Formula (I) are therefore effective in treating pathologies in which there is an appreciable effect of excessive production of NO from iNOS and similarly conventional NSAIDs in pathologies in which reduction of the inflammatory prostaglandins (e.g.: $PGE_2$) is pharmacologically useful, for instance in the treatment of arthritis, including but not limited to osteoarthritis, rheumatoid arthritis, neuropathic arthritis and systemic lupus erythematosus.

The compounds of the invention may also be particularly useful, by means of their inhibitory activity on the production of IL-6, for the treatment of gastrointestinal pathologies, for instance intestinal inflammations, Crohn's disease and ulcerative colitis. Finally, the compounds of the present invention may find use in the treatment of acute or chronic pain of articular or neuropathic origin, in conditions in which treatment with non-steroidal anti-inflammatory drugs (NSAIDs) or opiate analgesics is indicated.

The compounds of Formula (I) are represented by the following general formula:

Formula (I):

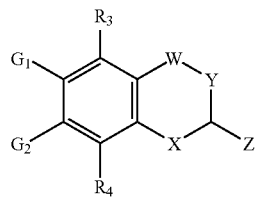

in which:
   $G_1$ and $G_2$ are independently selected from hydrogen, halogen, hydroxyl, $C_1$-$C_4$ alkoxy, $C_1$-$C_4$ alkyl, and the amidine substituent of formula Q, provided that, for each compound of formula (I), only one of the two substituents $G_1$ or $G_2$ is the amidine substituent of formula Q.

The amidine substituent of formula Q is represented by the structure given below, in which R is $C_1$-$C_4$ alkyl or cycloalkyl.

Amidine substituent of formula Q:

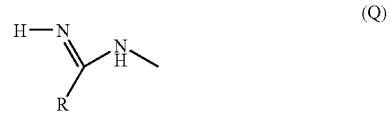

In the compounds of Formula I:
   W is independently: a bond, a substituted or unsubstituted carbon atom (=$CR_1$— or =CH—), an unsubstituted nitrogen atom (=N—);
   Y is a substituted or unsubstituted carbon atom (=$CR_1$— or =CH—), or an unsubstituted nitrogen atom (=N—);
   X is a substituted or unsubstituted carbon atom (=$CR_1$— or =CH—), a substituted or unsubstituted nitrogen atom (—$NR_2$— or =N—), a sulfur atom (—S—) or an oxygen atom (—O—); provided that: the substituents W, Y and X give rise, suitably in combination, to 9- or 10-membered bicyclic heteroaromatic derivatives containing up to 2 hetero atoms in the same ring, such as indole, benzofuran, benzothiophene, benzimidazole, benzoxazole, benzothiazole, quinoline, quinoxaline, quinazoline, isoquinoline or cinnoline derivatives.

The substituents $R_1$ and $R_2$ are independently selected from hydrogen, $C_1$-$C_4$ alkyl, $C_1$-$C_4$ alkenyl and $C_1$-$C_4$ alkoxy.

The substituents $R_3$ and $R_4$ are independently selected from hydrogen, halogen, hydroxyl, $C_1$-$C_4$ alkoxy, $C_1$-$C_4$ alkyl and $C_1$-$C_4$ alkenyl.

z is an aryl or heteroaryl group, or a linear or branched $C_1$-$C_6$ alkyl or alkenyl chain, or a $C_1$-$C_4$ alkyl-aryl group or a $C_1$-$C_4$ alkyl-heteroaryl group in which the aryl group is a phenyl which is unsubstituted or substituted with one or more substituents independently selected from halogen, trifluoromethyl, hydroxyl, nitro, cyano, carboxyl, carboxamido, carbonyl, thio, methylthio, methanesulfonyl, methanesulfinyl, sulfonamido, trifluoromethoxy, $C_1$-$C_6$ alkoxy and $C_1$-$C_6$ alkyl, and the heteroaryl group is a 5- or 6-atom heteroaromatic ring containing one or more hetero atoms, which is unsubstituted or substituted with one or more substituents independently selected from halogen, trifluoromethyl, hydroxyl, nitro, cyano, carboxyl, carbonyl, thio, methylthio, methanesulfonyl, methanesulfinyl, trifluoromethoxy, $C_1$-$C_6$ alkoxy and $C_1$-$C_6$ alkyl.

The $C_1$-$C_4$ alkyl-aryl group is a linear or branched, saturated or unsaturated $C_1$-$C_4$ hydrocarbon chain substituted with an aryl group. When the $C_1$-$C_4$ chain is unsaturated, it is intended to contain only one substituted or unsubstituted double bond. Substituents for the aryl group are independently selected from the groups defined above as substituents for the aryl group.

The $C_1$-$C_4$ alkyl-heteroaryl group is a linear or branched, saturated or unsaturated $C_1$-$C_4$ hydrocarbon chain substituted with a substituted or unsubstituted heteroaryl group. When the $C_1$-$C_4$ chain is unsaturated, it is intended to contain only one substituted or unsubstituted double bond.

The term "heteroaryl" means any of the heterocyclic nuclei defined above.

The compounds of formula (I) may thus be used either in free base form or as pharmaceutically acceptable salts. The present invention thus includes all the pharmaceutically acceptable salts of the compounds of formula (I). Pharmacologically acceptable salts of the compounds of formula (I) include, but are not limited to: hydrochloride, hydrobromide, sulfate, hydrogen sulfate, methanesulfonate, maleate, citrate, fumarate and succinate.

Pharmaceutical formulations of the compounds of the invention may be prepared using conventional techniques. The formulations include those suitable for oral, parenteral (including subcutaneous, intramuscular, intravenous, intra-articular and transdermal), topical or rectal use or other forms suitable for obtaining the desired therapeutic effect, for example delayed-action solid formulations for oral use allowing a slow release of the active principle over time.

Substances commonly used in the pharmaceutical field, such as excipients, binders, disintegrants and substances capable of stimulating transdermal or mucosal absorption, may be used together with the active principle in the pharmaceutical formulations.

Table 1 below, which is non-limiting, illustrates a number of compounds of formula (I) that are the subject of the present invention.

TABLE 1

Examples of compounds of formula (I)

| Compound | Structure | $G_1$ | $G_2$ | W | Y | X | Z |
|---|---|---|---|---|---|---|---|
| 1 | 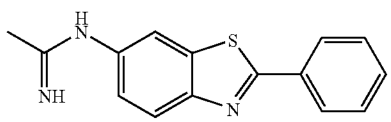 | Acetamidine | H | Bond | S | N | Ph |
| 3 | 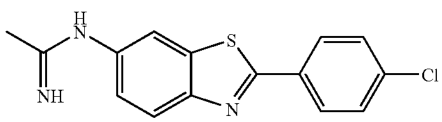 | Acetamidine | H | Bond | S | N | 4-Cl—Ph |
| 4 | 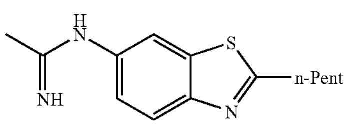 | Acetamidine | H | Bond | S | N | n-Pentyl |
| 5 | 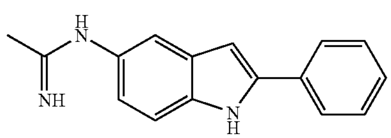 | Acetamidine | H | Bond | CH | NH | Ph |
| 6 | 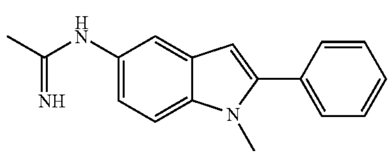 | Acetamidine | H | Bond | CH | NMe | Ph |
| 8 | 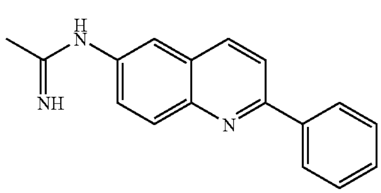 | Acetamidine | H | CH | CH | N | Ph |
| 9 | 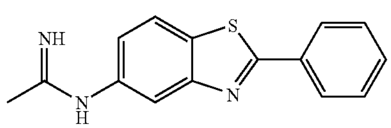 | H | Acetamidine | Bond | S | N | Ph |
| 10 | 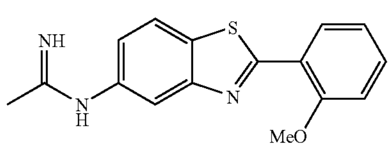 | H | Acetamidine | Bond | S | N | Ph |

TABLE 1-continued

Examples of compounds of formula (I)

| Compound | Structure | G₁ | G₂ | W | Y | X | Z |
|---|---|---|---|---|---|---|---|
| 11 | 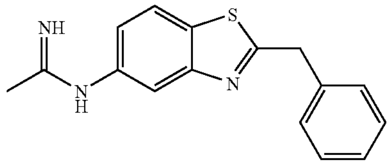 | H | Acetamidine | Bond | S | N | Benzyl |
| 12 | 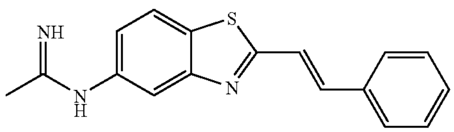 | H | Acetamidine | Bond | S | N | Styryl |
| 13 | 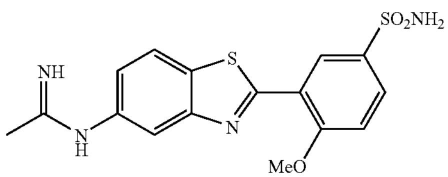 | H | Acetamidine | Bond | S | N | 2-MeO-5-SO₂NH₂—Ph |
| 14 | 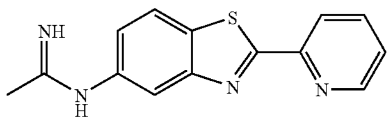 | H | Acetamidine | Bond | S | N | 2-pyridyl |
| 15 | 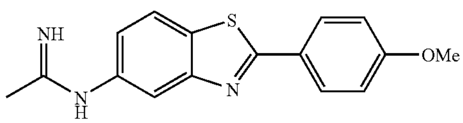 | H | Acetamidine | Bond | S | N | 4-MeO—Ph |
| 16 | 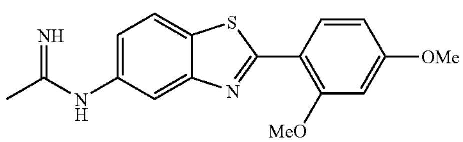 | H | Acetamidine | Bond | S | N | 2.4-(MeO)₂—Ph |
| 17 | 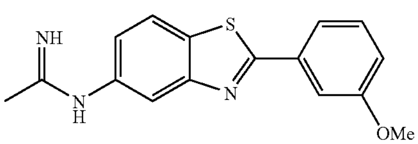 | H | Acetamidine | Bond | S | N | 3-MeO—Ph |
| 18 | 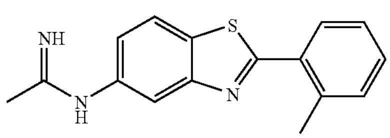 | H | Acetamidine | Bond | S | N | 2-Me—Ph |
| 19 | 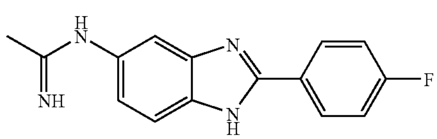 | Acetamidine | H | Bond | N | NH | 4-F—Ph |
| 20 | 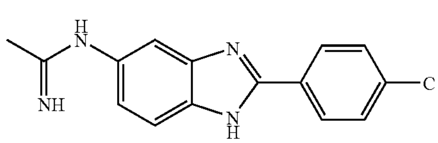 | Acetamidine | H | Bond | N | NH | 4-Cl—Ph |

TABLE 1-continued

Examples of compounds of formula (I)

| Compound | Structure | G$_1$ | G$_2$ | W | Y | X | Z |
|---|---|---|---|---|---|---|---|
| 21 | 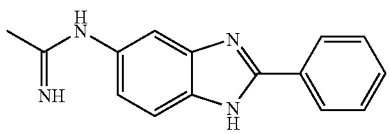 | Acetamidine | H | Bond | N | NH | Ph |
| 22 | 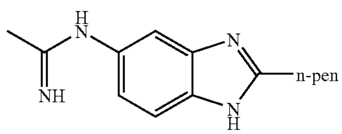 | Acetamidine | H | Bond | N | NH | n-pentyl |
| 23 | 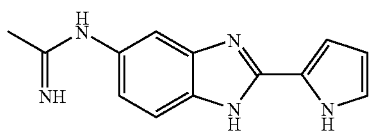 | Acetamidine | H | Bond | N | NH | 2-pyrrol |
| 25 | 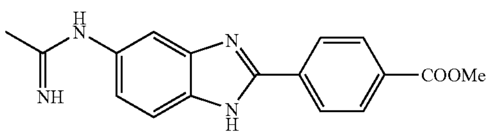 | Acetamidine | H | Bond | N | NH | 4-CO$_2$Me—Ph |
| 26 | 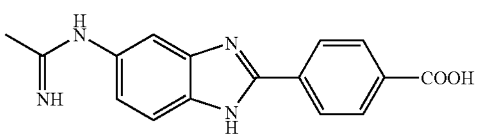 | Acetamidine | H | Bond | N | NH | 4-CO$_2$H—Ph |
| 27 | 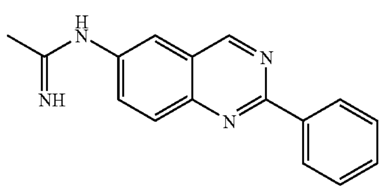 | Acetamidine | H | CH | N | N | Ph |
| 28 | 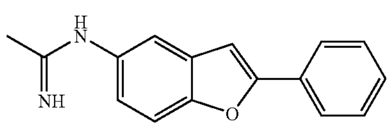 | Acetamidine | H | Bond | CH | O | Ph |
| 29 | 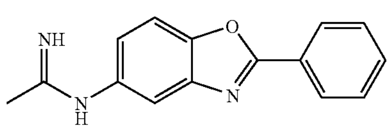 | H | Acetamidine | Bond | O | NH | Ph |
| 30 | 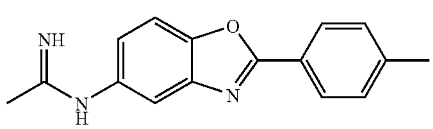 | H | Acetamidine | Bond | O | NH | 4-ClPh |
| 31 | 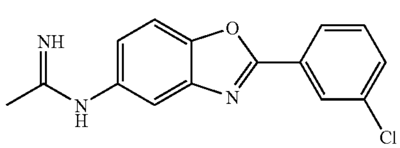 | H | Acetamidine | Bond | O | NH | 3-CF$_3$ Ph |

TABLE 1-continued

Examples of compounds of formula (I)

| Compound | Structure | G₁ | G₂ | W | Y | X | Z |
|---|---|---|---|---|---|---|---|
| 32 | 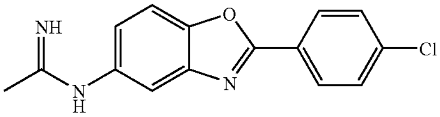 | H | Acetamidine | Bond | O | NH | 4-CF₃ Ph |
| 33 | 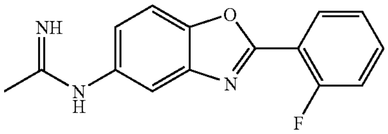 | H | Acetamidine | Bond | O | NH | 2-FPh |
| 34 | 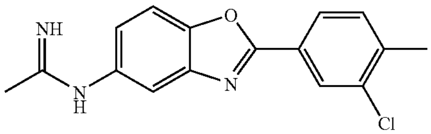 | H | Acetamidine | Bond | O | NH | 3,4-Cl Ph |
| 35 | 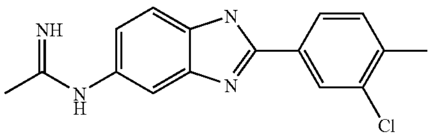 | H | Acetamidine | Bond | N | NH | 3,4-Cl Ph |
| 36 | 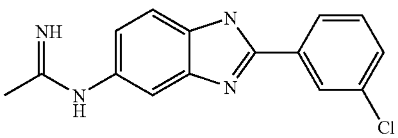 | H | Acetamidine | Bond | N | NH | 3-CF₃ Ph |
| 37 | 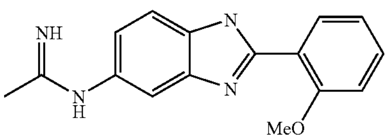 | H | Acetamidine | Bond | N | NH | 2-OMe Ph |
| 38 | 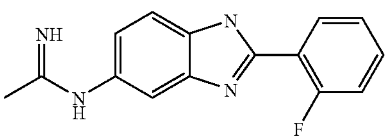 | H | Acetamidine | Bond | N | NH | 2-FPh |
| 39 | 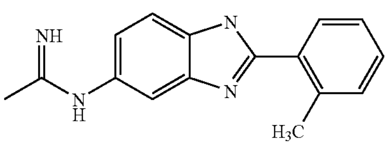 | H | Acetamidine | Bond | N | NH | 2-Me Ph |
| 40 | 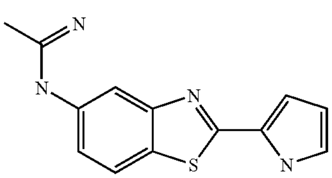 | Acetamidine | H | Bond | S | N | 2-pyrrol |
| 41 | | | | H | Bond | S | N | 2-Ph |

TABLE 1-continued

Examples of compounds of formula (I)

| Compound | Structure | G₁ | G₂ | W | Y | X | Z |
|---|---|---|---|---|---|---|---|
| 42 | 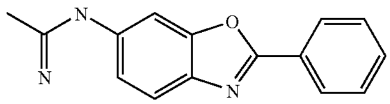 | Acetamidine | H | Bond | O | NH | Ph |
| 43 | 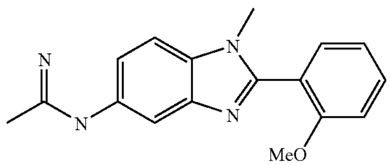 | H | Acetamidine | Bond | NR | N | 2-MeO—Ph |
| 44 | 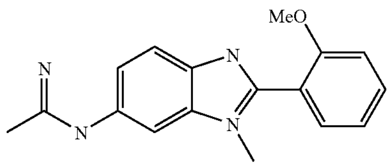 | H | Acetamidine | Bond | N | NR | 2-MeO—Ph |

According to a further aspect of the present invention, the process required for preparing the compounds of formula (I) is described.

The compounds of the invention are prepared from a compound of formula (II) by reaction with a compound of formula (III).

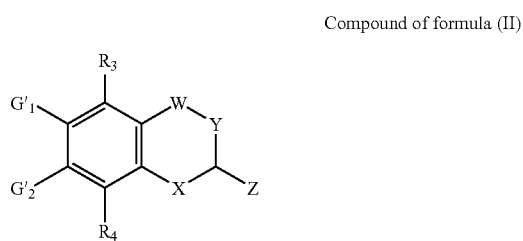

Compound of formula (II)

in which W, Y, X, z, R₃ and R₄ are defined as for the compounds of formula (I), while G'₁ and G'₂ are independently selected from: hydrogen, halogen, hydroxyl, $C_1$-$C_4$ alkoxy, $C_1$-$C_4$ alkyl, and the amine group (—NH₂), provided that, for each compound of formula (II), only one of the substituents G'₁ or G'₂ is an amine group (—NH₂).

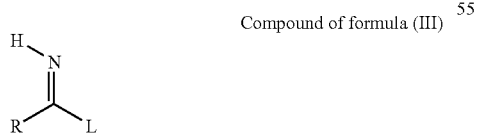

Compound of formula (III)

in which R is as defined for the amidino substituent of formula Q and L is a leaving group. The leaving group L is an alkoxy group (ethoxy or methoxy), or an alkylthio group (RS—; thiomethyl or thiomethylnaphthyl) or an arylthio group (Ar—S; thiophenyl).

Optionally, the following steps can complete the conversion of a compound of formula (II) into a compound of formula (I):
removal of any protecting group present
conversion of the product into the corresponding salt or solvate.

The reaction of a compound of formula (II) with a compound of formula (III) may be performed in a suitable solvent such as: alcohol, acetonitrile, N,N-dimethylformamide (DMF) or tetrahydrofuran (THF), at temperatures of between 0° C. and 50° C., as described in the case of alkoxy-imidates (Cereda et al., J. Med. Chem., 1990, 33, 2108-2113) or in the case of thioimidates (Collins et al., J. Med. Chem., 1998, 41, 2858-2871; Miosokowski et al., Synthesis, 1999, 6, 927-929; J. Eustache et al. Tetrahedron Letters, 1995, 36, 2045-2046, or Shearer et al., Tetrahedron Letters, 1997, 38, 179-182).

The compounds of formula (III) are commercially available or may be prepared as described in the given references.

The compounds of formula (II) are obtained from compounds of formula (IV):

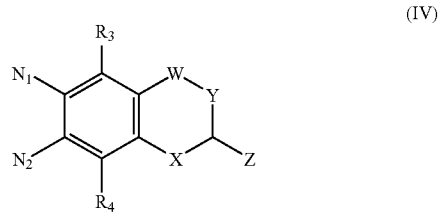

(IV)

in which W, Y, X, z, R₃ and R₄ are as defined above for the compounds of formula (I), N₁ and N₂ are independently selected from: hydrogen, halogen, hydroxyl, $C_1$-$C_4$ alkoxy, $C_1$-$C_4$ alkyl, nitro group (NO₂), or protected amine group (e.g. carbamate or amide), or a suitable precursor of an amine group, for instance a carboxyl (COOH) or a derivative thereof (acyl chloride, ester or primary amide), provided that, for each compound of formula (IV), only one of the substituents $N_1$ or $N_2$ is a nitro group or a protected amine group, or a suitable precursor thereof as defined above. Suitable protecting groups for the amine group include: t-butoxycarbonyl (BOC), benzyloxycarbonyl (z), trifluoroacetyl, acetyl and benzoyl.

When $N_1$ or $N_2$ is a nitro group, the compounds of formula (II) are obtained by reducing a compound of formula (IV). The reduction may be performed either using hydrogen and a catalyst (Pd/C or $PtO_2$), according to the usual methods of organic chemistry (P. Rylander, *Catalytic Hydrogenation in Organic Synthesis*, Academic Press, 1979), or using chemical reducing agents, for instance stannous chloride (F. D. Bellamy et al., Tetrahedron Letters, 1984, 25 (8), 839-842.), iron (C. A. Merlic, JOC, 1995, 33-65), nickel boride (Atsuko Nose, Chem. Pharm. Bull., 1989, 37, 816-818), Raney nickel/propanol (Kuo E., Synthetic Communication, 1985, 15, 599-6023) or sodium borohydride and Pd/C (Petrini M., Synthesis, 1987, 713-714).

When $N_1$ or $N_2$ is a protected amine group, the compounds of formula (II) may be obtained from a compound of formula (IV) by removal of the protecting group, according to methods known in organic chemistry (T. W. Green and P. Wuts, *Protective Groups in Organic Synthesis*, 1991, J. Wiley & Sons).

When $N_1$ or $N_2$ is a carboxyl group (COOH), the conversion of a compound of formula (IV) into a compound of formula (II) may be performed via Schmidt or Curtius degradation (H. Wolff, Organic Reactions, 1946.3, 307; J. Saunders, Chem. Rev. 1948, 43, 203).

The compounds of formula (IV) are commercially available or may be prepared from compounds of formula (V):

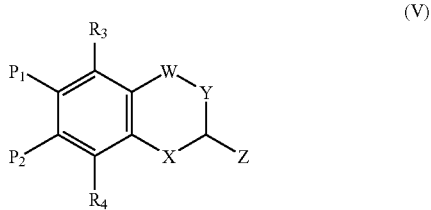

(V)

in which:

a) W, Y, X, z, $R_3$ and $R_4$ are as defined for the compounds of formula (I) and $P_1$ and $P_2$ are independently selected from hydrogen, halogen, hydroxyl, $C_1$-$C_4$ alkoxy and $C_1$-$C_4$ alkyl, provided that, for each compound of formula (V), at least one of the substituents $P_1$ or $P_2$ is a hydrogen atom. In this case, the compounds of formula (IV) may be obtained by aromatic nitration of a compound of formula (V) and, where applicable, by separation of the desired product from the corresponding regioisomers.

b) W, Y, X, $R_3$ and $R_4$ are defined as for the compounds of formula (I), z is a halogen or hydrogen, and $P_1$ and $P_2$ are independently selected from groups as defined in a) and also nitro, amine and protected amine, provided that, for each compound of formula (V), only one of the substituents $P_1$ or $P_2$ is a nitro group, an amine group or a protected amine group. In this case, a compound of formula (V) may be converted into a compound of formula (IV) in which z is aryl or heteroaryl via formation of an aromatic-aromatic bond according to standard methods of organic chemistry (from J. Hassan, Chem. Rev., 2002, 102, 1359-469); when, in the compounds of formula (IV), z is an aryl or heteroaryl group, the compounds of formula (V) are converted into compounds of formula (IV), using the coupling of an aryl-zinc with a suitable halide or the Stille reaction of the appropriate stannane with the corresponding halide.

When, in the compounds of formula (V), z is halogen, and, in the compounds of formula (IV), z is an aryl or heteroaryl group, the corresponding conversion may be performed by using the coupling of zinc derivatives with aromatic or heteroaromatic halides (Scheme 1).

According to this method, the compounds of formula (V), in which z is H or halogen, are reacted with n-butyllithium or t-butyllithium, the resulting organolithium derivative (Va) is reacted with zinc chloride to give the corresponding organozinc reagents (Vb), which are reacted with the aryl or heteroaryl halide, via homogeneous catalysis (palladium), to form the compounds of formula (IV).

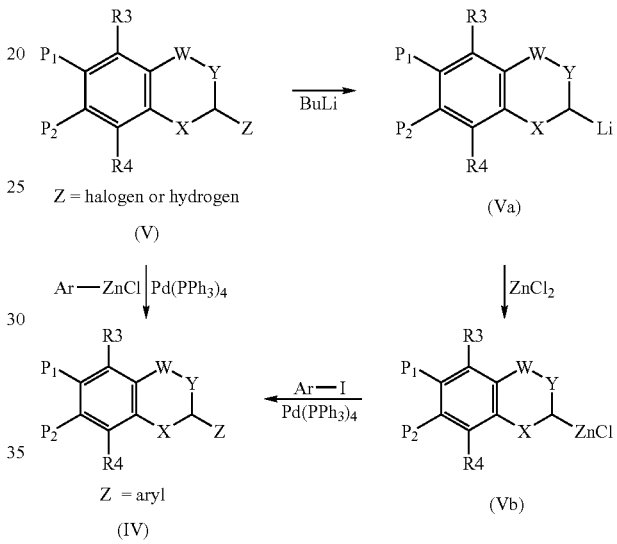

The reaction conditions are equivalent to those reported (M. Amat et al., J. Org. Chem., 1997, 62, 3158 and S. Hargreaves et al., Tetrahedron Letters, 2000, 41, 1653). Alternatively, the intermediates (Vb, Scheme 1) may be obtained directly from the compounds of formula (V) by oxidative addition of zinc metal (Knochel et al., Tetrahedron Lett., 1990, 31, 4413; Yamanaka et al., Tetrahedron, 1993. 49, 9713).

Alternatively, the compounds of formula (IV) are obtained from compounds of formula (V) in which z is halogen (Scheme 1) by reaction with an aryl or heteroaryl zinc derivative, using methods identical to those mentioned previously.

Alternatively (Scheme 2), when, in the compounds of formula (V), z is hydrogen or halogen, and, in the compounds of formula (IV), z is an aryl or heteroaryl group, the conversion of (V) into (IV) may be performed via cross-coupling catalysed by Pd stannanes with aryl or heteroaryl halides, according to the Stille method. The compounds of formula (V) in which z is halogen are converted into the corresponding aryl-stannanes (Vb) according to known methods (Pereyere M., *Tin in Organic Synthesis*, Butterworths, 1987), i.e. by reacting a compound of formula (V) in which z is halogen with hexamethylditin, using tetrakis(triphenylphosphine)palladium (0) as catalyst, in refluxing THF (J. La Voie, J. Org. Chem., 2000, 65, 2802-2805) or by reaction with hexabutylditin using the same catalyst, in toluene as solvent (K. Masanori et al., Bull. Chem. Soc. Jpn, 1983, 56, 3855-3856). This method is particularly effective when, in the compounds of formula (V), $P_1$ or $P_2$ is a nitro group or in which other substituents do not support the presence of bases and/or nucleophiles such as alkyllithiums.

Alternatively (Scheme 2), the compounds of formula (IV) may be obtained from compounds of formula (V) in which z is halogen or hydrogen by reaction with an organolithium (n-butyllithium or t-butyllithium). In this case, the compounds of formula (V) give the corresponding derivatives (Va), which are reacted with trimethyltin chloride or tri-n-butyltin chloride to give the corresponding stannanes (Vb). These intermediates are reacted with suitable aromatic or heteroaromatic halides, under palladium catalysis, to give the compounds of formula (IV). The conversion of compounds of formula (V) into compounds of formula (Vb) may be performed using known procedures (P. Jutzi, J. Organometallic Chem., 1983, 246, 163-168). The coupling of the stannanes (Vb) with aromatic or heteroaromatic halides is performed according to standard procedures (P. Gros, Synthesis, 1999, 5, 754-756).

Alternatively, the compounds of formula (IV) are obtained from compounds of formula (V) in which z is halogen (Scheme 2), via palladium-catalysed coupling with an aryl or heteroaryl stannane, using the methods described above, the preferred route depending on the compatibility of the substituents present.

pounds of formula (V), in which z is hydrogen or halogen, via Suzuki coupling of boronic derivatives with the corresponding halides. This palladium-catalysed reaction for formation of the aryl-aryl bond using arylboronic or heteroarylboronic derivatives is a known process (J. Hassan, 2002, Chem Rev., 102, 1359-1469).

In this case, compounds of formula (V), in which z is hydrogen or halogen, are converted into the boronates (Vb) by reaction with an alkyllithium or lithium diisopropylamide to form the intermediates (Va), which are converted into the boronates (Vb) by reaction with trimethyl or triisopropyl borate according to standard procedures (A. Alvarez, J. Org. Chem., 1992, 57, 1653-1656, o J. G. Grieb, Synthetic Commun., 1995, 25, 214-2153).

The palladium-catalysed coupling of the intermediates (Vb), boronic acids or esters, with suitable aryl halides gives the compounds of formula (IV), according to known procedures (B. Maes et al., Tetrahedron, 2000, 56, 1777-1781).

Alternatively, the compounds of formula (IV) are obtained from the compounds of formula (V) in which z is halogen (Scheme 3) via Suzuki coupling with an aryl or heteroaryl boronic derivative, using the same methods as mentioned above.

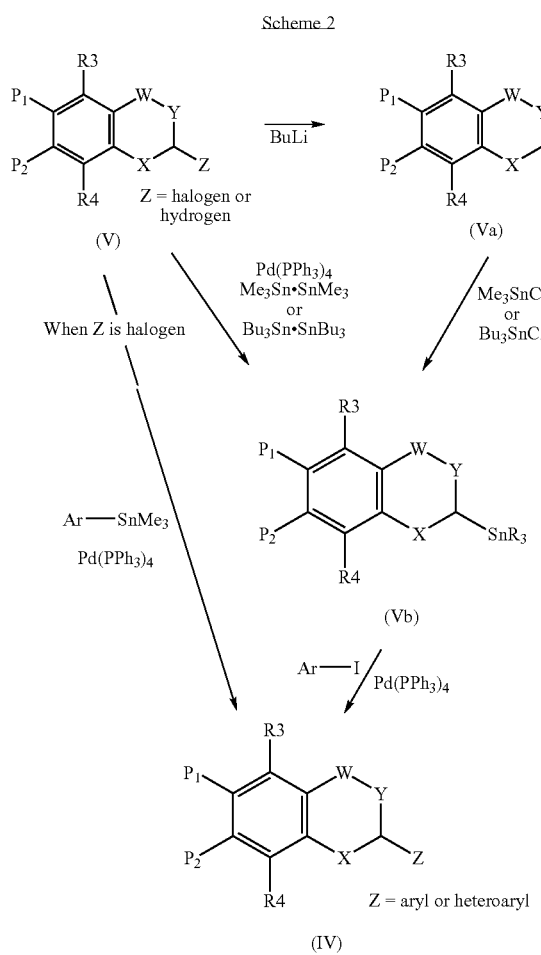

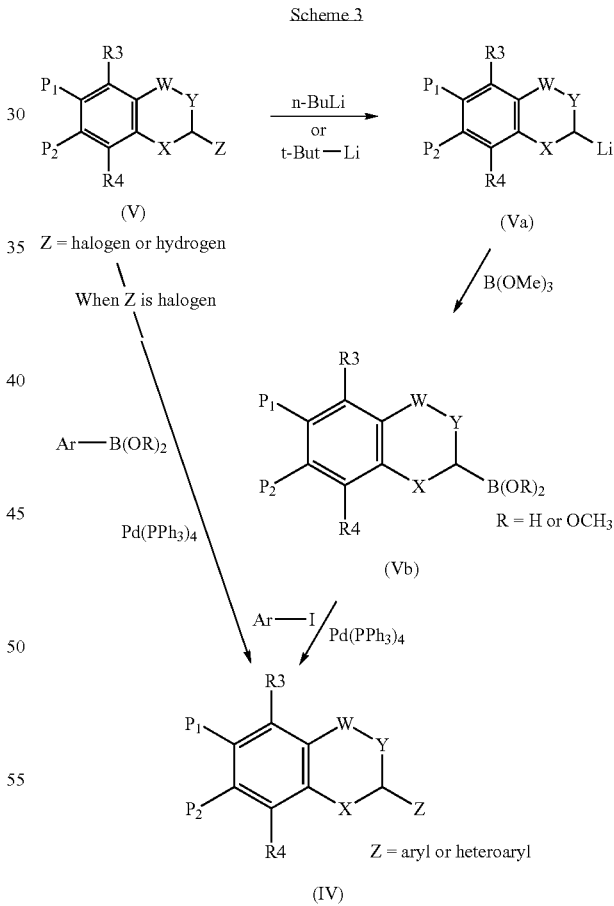

Alternatively (Scheme 3), the compounds of formula (IV) in which z is aryl and heteroaryl may be obtained from compounds Alternatively (Scheme 4), the compounds of formula (IV) in which W, Y, X, $R_3$ and $R_4$ are defined as for the compounds of formula (I), z is a linear or branched $C_1$-$C_6$ chain, a $C_1$-$C_4$ alkylaryl group or a $C_1$-$C_4$ alkylheteroaryl group, $P_1$ and $P_2$ are as defined in point (b), and are obtained from the esters of formula (V) via Heck synthesis. In this case, the compounds of formula (V) in which z is a suitable halogen are converted into compounds of formula (IV) in which z is a linear or branched $C_1$-$C_6$ alkenyl chain, a $C_1$-$C_4$ alkenylaryl group or a $C_1$-$C_4$ alkenylheteroaryl group via palladium-catalysed arylation of a terminal olefin (Heck reaction). The resulting olefins may constitute per se compounds of formula (IV) or may be converted (reduction reaction of the olefin to a saturated hydrocarbon) into compounds of formula (IV) in which z is a linear or branched $C_1$-$C_6$ alkyl chain, a $C_1$-$C_4$ alkyl-aryl group or a $C_1$-$C_4$ alkylheteroaryl group. The Heck reaction is performed according to known procedures (R. F. Heck, Org. React., 1982, 27, 345-390). In the case where the compound of formula (IV) thus obtained, in which z is a linear or branched, unsaturated $C_1$-$C_6$ chain, needs to be converted into a compound of formula (IV) in which z is a saturated $C_1$-$C_6$ chain, via catalytic hydrogenation, common techniques are used (P. Rylander, *Catalytic Hydrogenation in organic Synthesis*, Academic Press, 1979).

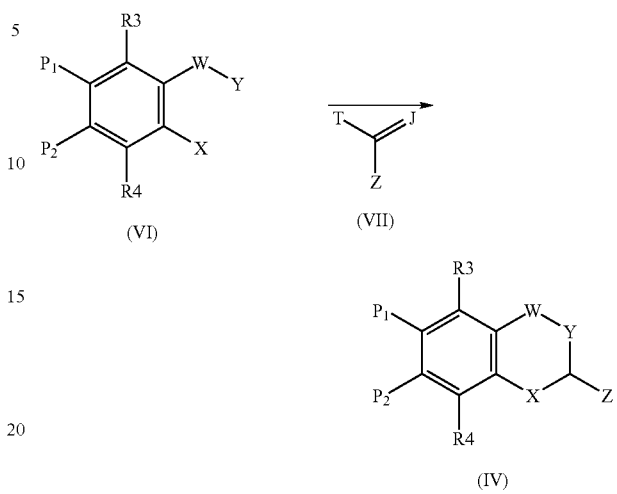

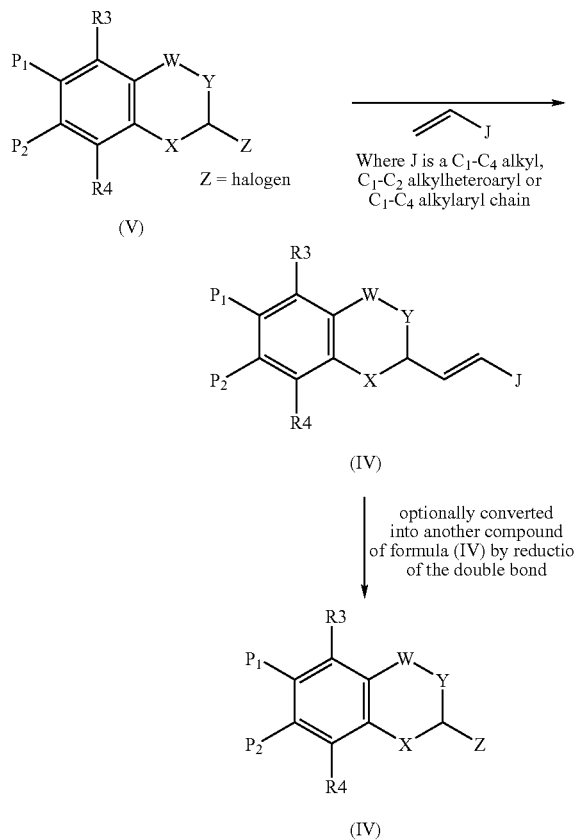

For the compounds of formula (VII), z is as defined for the compounds of formula (I), J is an oxygen atom (O) or a nitrogen atom (N) and T is hydroxyl, hydrogen, halogen, amine or $C_1$-$C_4$ alkoxy.

Non-limiting examples of the synthetic route (c) are given in Scheme 6 below:

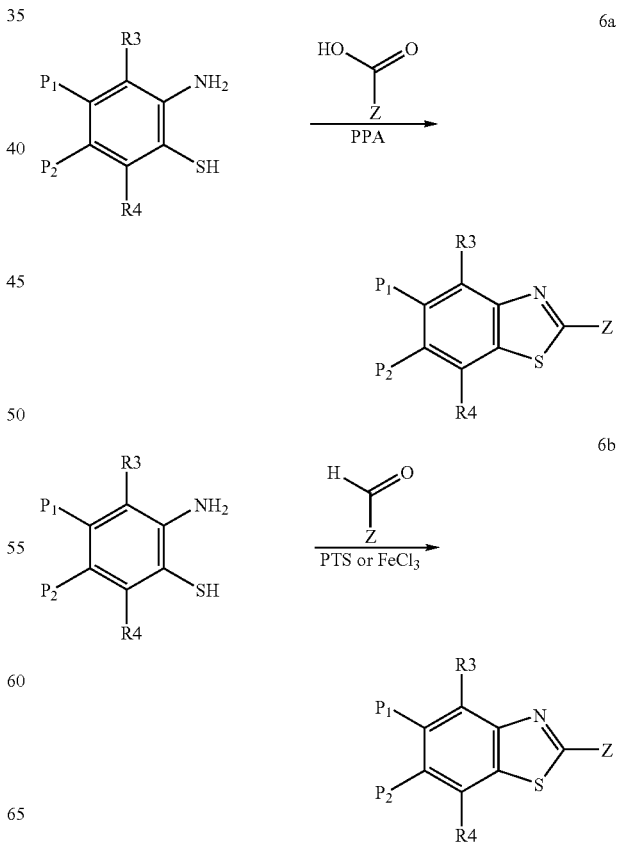

c) Alternatively (Scheme 5), the compounds of formula (IV), in which: W, Y, X, z, $R_3$ and $R_4$ are as defined for the compounds of formula (I), $P_1$ and $P_2$ are as defined in point (b), are prepared by reaction of a compound of formula (VI) with a compound of formula (VII). In the case where, for the compounds of formula (VI), $P_1$ and $P_2$ are as defined above, W is a bond or a substituted or unsubstituted carbon atom, as defined previously. Y is a thiol group (SH), a hydroxyl group (OH), an unsubstituted nitrogen atom, (—$NH_2$) or a triphenyl-phosphonium group $P^+(Ph)_3$, X is a substituted or unsubstituted nitrogen atom (—$NH_2$ or —$NHR_2$), a thiol group (—SH) or a hydroxyl group (—OH).

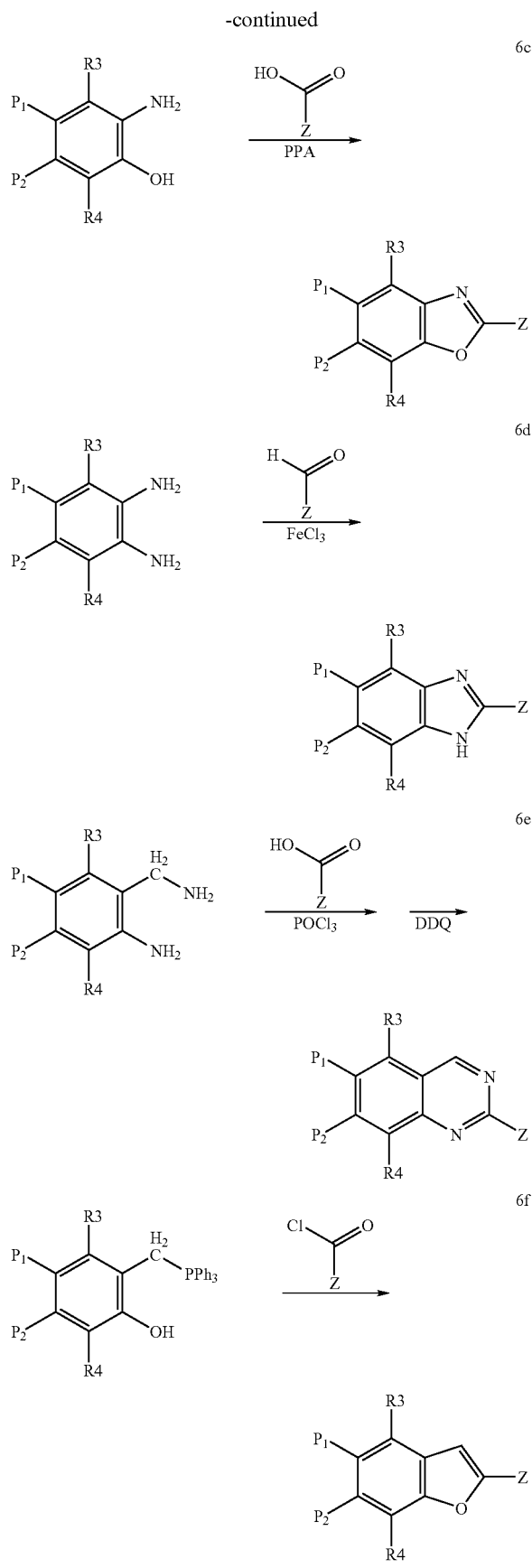
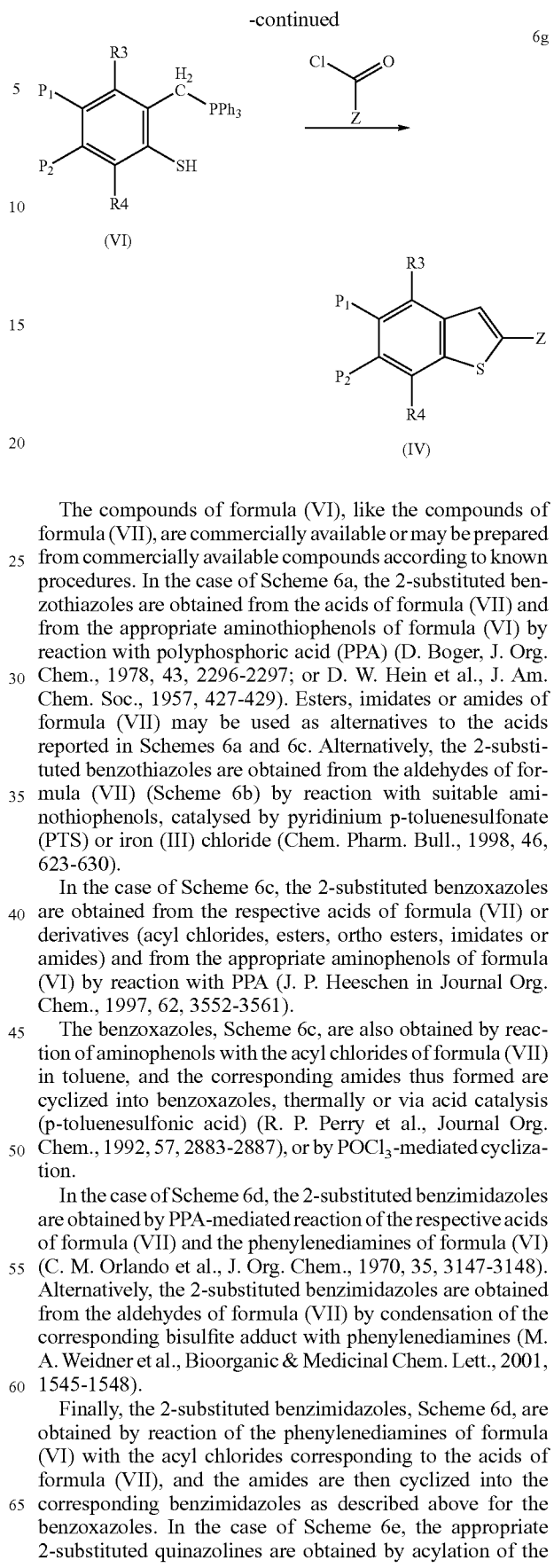

The compounds of formula (VI), like the compounds of formula (VII), are commercially available or may be prepared from commercially available compounds according to known procedures. In the case of Scheme 6a, the 2-substituted benzothiazoles are obtained from the acids of formula (VII) and from the appropriate aminothiophenols of formula (VI) by reaction with polyphosphoric acid (PPA) (D. Boger, J. Org. Chem., 1978, 43, 2296-2297; or D. W. Hein et al., J. Am. Chem. Soc., 1957, 427-429). Esters, imidates or amides of formula (VII) may be used as alternatives to the acids reported in Schemes 6a and 6c. Alternatively, the 2-substituted benzothiazoles are obtained from the aldehydes of formula (VII) (Scheme 6b) by reaction with suitable aminothiophenols, catalysed by pyridinium p-toluenesulfonate (PTS) or iron (III) chloride (Chem. Pharm. Bull., 1998, 46, 623-630).

In the case of Scheme 6c, the 2-substituted benzoxazoles are obtained from the respective acids of formula (VII) or derivatives (acyl chlorides, esters, ortho esters, imidates or amides) and from the appropriate aminophenols of formula (VI) by reaction with PPA (J. P. Heeschen in Journal Org. Chem., 1997, 62, 3552-3561).

The benzoxazoles, Scheme 6c, are also obtained by reaction of aminophenols with the acyl chlorides of formula (VII) in toluene, and the corresponding amides thus formed are cyclized into benzoxazoles, thermally or via acid catalysis (p-toluenesulfonic acid) (R. P. Perry et al., Journal Org. Chem., 1992, 57, 2883-2887), or by $POCl_3$-mediated cyclization.

In the case of Scheme 6d, the 2-substituted benzimidazoles are obtained by PPA-mediated reaction of the respective acids of formula (VII) and the phenylenediamines of formula (VI) (C. M. Orlando et al., J. Org. Chem., 1970, 35, 3147-3148). Alternatively, the 2-substituted benzimidazoles are obtained from the aldehydes of formula (VII) by condensation of the corresponding bisulfite adduct with phenylenediamines (M. A. Weidner et al., Bioorganic & Medicinal Chem. Lett., 2001, 1545-1548).

Finally, the 2-substituted benzimidazoles, Scheme 6d, are obtained by reaction of the phenylenediamines of formula (VI) with the acyl chlorides corresponding to the acids of formula (VII), and the amides are then cyclized into the corresponding benzimidazoles as described above for the benzoxazoles. In the case of Scheme 6e, the appropriate 2-substituted quinazolines are obtained by acylation of the amines (VI) with the benzoic acids (VII), followed by POCl$_3$-mediated cyclization (A. Downes, in J. Chem Soc., 1950, 3053-3055), and the synthesis is completed by oxidation with DDQ or chloranil; the procedure described by J. Van den Eynde, Synthesis, 1993, 867-869 may be used as an alternative.

In the case of Scheme 6f, the benzofuran derivatives of formula (IV) are prepared by reaction of the corresponding phosphoranes, obtained from the phosphonium salts of formula (VI) and from the acyl chlorides of formula (VII). In the case of Scheme 6g, the benzothiophene derivatives of formula (IV) are prepared by reaction of the corresponding phosphoranes obtained from phosphonium salts of formula (VI) and from the acyl chlorides of formula (VII)(A. Arnoldi, M. Carughi., Synthesis, 1988, 155-157).

d) Alternatively (Scheme 7), the compounds of formula (IV) in which: W, Y, X, z, R$_3$ and R$_4$ are as defined for the compounds of formula (I), and P$_1$ and P$_2$ are as defined in point (b), are prepared by cyclization reaction of a compound of formula (XIII). The compounds of formula (XIII) are prepared by reaction of a compound of formula (XII) with the compounds of formula (XI). In the case where, for the compounds of formula (XI), P$_1$ and P$_2$, R$_3$ and R$_4$ are as defined above, X is a hydrogen atom, a nitrogen atom, a carboxylate group (COOH) or a derivative thereof, or an aldehyde group (CHO); T is a halogen or a sulfur atom. In the compounds of formula (XIII), w is a sulfur atom, a substituted carbon atom (—CR$_1$=) or an unsubstituted carbon atom (—CH=) belonging to an olefinic or acetylenic system; Y is a substituted or unsubstituted carbon atom and z is defined as for the compounds of formula (I).

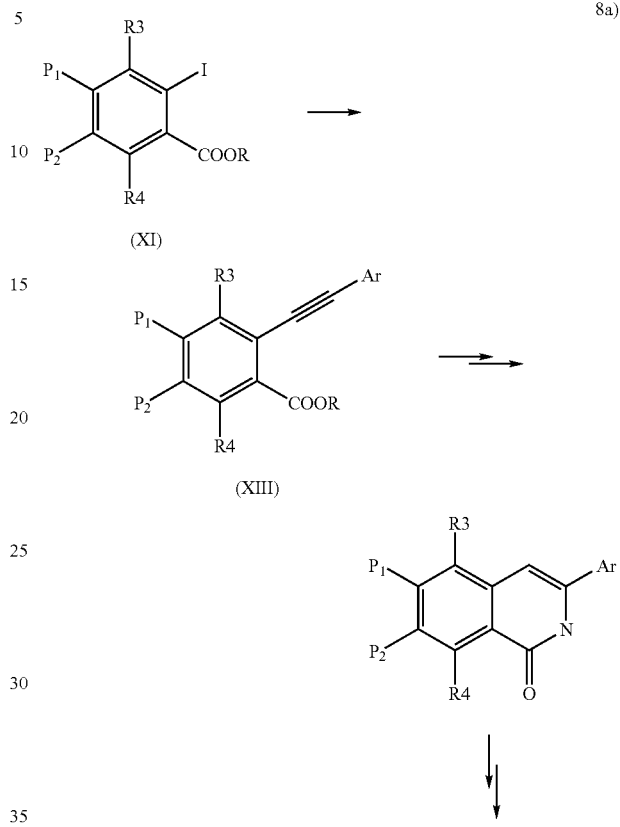

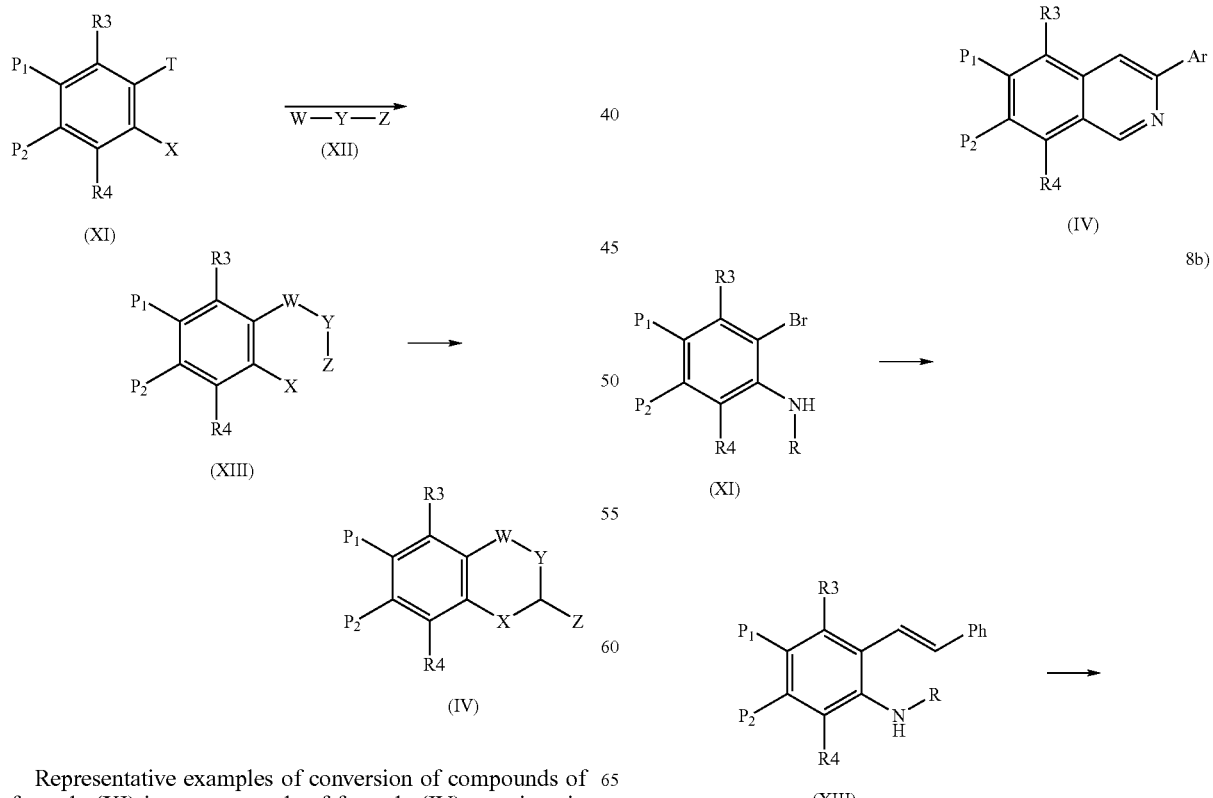

Representative examples of conversion of compounds of formula (XI) into compounds of formula (IV) are given in Scheme 8.

-continued

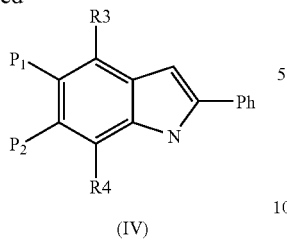

(IV)

In Scheme 8a), the 2-iodobenzoic derivative, a compound of formula (XI), is converted into the acetylenic derivative of formula (XIII), via a Heck reaction (R. C. Larock et al., Journal Org. Chem., 2003, 68, 5936). The compound of formula (XIII) is then cyclized into the isocoumarin, which, by reaction with methanolic ammonia, is converted into the corresponding isoquinolinone; the isoquinolinone is converted into the compound of formula (IV) via known methods, for example by conversion to 1-chloroisoquinoline, followed by reductive dehalogenation.

As reported in Scheme 8b), the 2-bromoaniline of formula (XI) is reacted, under Heck conditions, with styrene or with a substituted styrene to give the compounds of formula (XIII) in which W and Y are both carbon atoms forming part of an olefinic bond. The cyclization of the compound of formula (XIII) into the compound of formula (IV) is performed via catalysis with Pd (J. LaVoie, Bio-organic & Medicinal Chem., 1996, 4, 621-630).

The following non-limiting examples describe the details of the synthesis of the amidine derivatives of formula (I):

EXAMPLES OF PREPARATION OF COMPOUNDS OF FORMULA (I) ACCORDING TO SYNTHETIC ROUTE (a)

Example 1

Compound 1

N-(2-phenylbenzothiazol-6-yl)acetamidine

Triethylamine (36.7 ml, 0.263 mol) is added to methyl acetamidate hydrochloride (28.85 g, 0.263 mol) in acetonitrile (600 ml). The mixture is stirred at room temperature for 15 minutes and 2-phenyl-6-aminobenzothiazole (29.8 g, 0.131 mol) is added. The resulting mixture is stirred for 72 hours at room temperature, the solid is filtered off, suspended in ethyl acetate and basified with 1M NaOH (pH=10), and the phases are separated. The organic phase is washed with water, dried and evaporated. The solid is recrystallized from isopropyl ether. Yield: 14.5 g (42%); Elem. anal. $C_{15}H_{13}N_3S$; theory: C, 67.39; H, 4.90; N, 15.72. found C, 66.78; H, 5.03; N, 15.60. IR (KBr): 3260, 3020, 1645, 1590 cm$^{-1}$; $^1$H-NMR ($d_6$-DMSO) 8.05 (m, 2H); 7.9 (d, 1H); 7.35-7.55 (m, 3H); 6.95 (m, 1H); 5.9-6.2 (broad s, 2H); 1.8 (m, 3H).

1a) 2-phenyl-6-aminobenzothiazole

2-Phenyl-6-nitrobenzothiazole (73.5 g, 0.286 mol) is added to tin dichloride (200.74 g, 0.89 mol) in 37% HCl (300 ml). The mixture is heated at 100° C. for 40 minutes. The resulting mixture is cooled and aqueous ammonia (pH=10) is added dropwise. The product is extracted with chloroform and the extracts are concentrated. The solid is recrystallized from isopropyl ether/hexane (2/1). Yield: 29.9 g (46%); Rf (9/1 chloroform/methanol): 0.68; m.p.: 199.8-201.1° C.; IR (KBr): 3450, 3305, 3190, 1619 cm$^{-1}$.

1b) 2-phenyl-6-nitrobenzothiazole

2-Phenylbenzothiazole (Aldrich, 63.89 g, 0.302 mol) is nitrated with 100% nitric acid (190 ml, 4.53 mol) at 5° C. The mixture is stirred at 5° C. for 70 minutes, quenched in ice-water and basified with 32% NaOH (pH=10). The product is filtered off and the solid obtained is suspended in water and filtered off. The product is recrystallized from isopropyl ether. Yield: 73.6 g (95%); Rf (8/2 petroleum ether/ethyl acetate): 0.76; m.p.: 178.9-181.3°; $^1$H-NMR ($d_6$-DMSO): 9.16 (d, 1H); 8.35 (dd, 1H); 8.23 (d, 1H); 8.15 (dd, 1H) 7.58; (m, 4H).

Example 2

Maleate of Compound 1-Compound 2

N-(2-phenylbenzothiazol-6-yl)acetamidine maleate

A 1M solution of maleic acid in acetone (10 ml) is added dropwise to N-(2-phenylbenzothiazol-6-yl)acetamidine (1 g, 0.00374 mol) (Example 1), in acetone (30 ml). The product is precipitated and filtered off. Yield: 1.09 g (77%); Elem. anal. $C_{15}H_{13}N_3S \cdot C_4H_4O_4$; theory C, 59.51; H, 4.47; N, 10.96. found C, 59.30; H, 4.36; N, 10.62. IR (KBr): 3060, 1700, 1480, 1360 cm$^{-1}$.

Example 3

Compound 3

N-[2-(4-chlorophenyl)benzothiazol-6-yl]acetamidine

Prepared in a manner similar to that of Example 1. Yield: 40%; Elem. anal. $C_{19}H_{17}N_3O_4S$; M.W.: 383.419; theory C, 59.70; H, 4.00; N, 13.92. found C, 59.29; H, 3.70; N, 13.63. IR (KBr): 3450, 3290, 3115, 1640 cm$^{-1}$; $^1$H-NMR ($d_6$-DMSO): 8.2 (d, 2H); 7.9 (m, 1H); 7.6 (d, 2H); 7.4 (m, 1H); 6.9 (m, 1H); 6.3 (broad s, 2H); 1.9 (m, 3H).

3a) 2-(4-chlorophenyl)-6-aminobenzothiazole

Prepared in a manner similar to that of Example 1a. Yield: 77%; Rf (8/2 hexane/ethyl acetate): 0.16; m.p.: 165.9-168° C.; Elem. anal. $C_{13}H_9ClN_2S$; theory C, 59.88; H, 3.48; N, 10.74. found C, 59.22; H, 3.34; N, 10.84. IR (KBr): 3460, 3355, 3195, 1620 cm$^{-1}$.

3b) 2-(4-chlorophenyl)-6-nitrobenzothiazole

Prepared in a manner similar to that of Example 1b from 2-(4-chlorophenyl)benzothiazole, which is prepared in a manner similar to that of Example 4c. Yield: 84%; Rf (3/7 chloroform/toluene): 0.50; m.p.: 227.2-232° C.; IR (KBr): 1515, 1340 cm$^{-1}$; $^1$H-NMR ($d_6$-DMSO): 9.16 (d, 1H); 8.35 (dd, 1H); 8.23 (d, 1H); 8.15 (dd, 1H); 7.58 (m, 4H).

Example 4

Compound 4

N-(2-pentylbenzothiazol-6-yl)acetamidine

Triethylamine (16.6 ml, 0.119 mol) is added to methyl acetamidate hydrochloride (5.58 g, 0.051 mol) in acetonitrile (100 ml). The mixture is stirred at room temperature for 15 minutes, and 2-pentyl-6-aminobenzothiazole (hydrochloride) (8.9 g, 0.034 mol) is added. The resulting mixture is stirred at room temperature for 48 hours, filtered and evaporated. The residue is taken up in ethyl acetate and the product is extracted with 0.1M HCl. The aqueous phases are combined, basified with NaOH (pH=10) and extracted with ethyl acetate. The extracts are washed with water. The resulting organic phase is dried, filtered and evaporated. The solid is recrystallized from isopropyl ether. Yield: 5.0 g (56%); Elem. anal. $C_{14}H_{19}N_3S$; M.W.: 261.39; theory C, 64.33; H, 7.32; N, 16.07. found C, 64.42; H, 7.48; N, 16.13. IR (KBr): 3318, 3085, 1655, 1615, 1586 $cm^{-1}$; $^1$H-NMR ($d_6$-DMSO) 7.7 (d, 1H); 7.3 (m, 1H); 6.8 (m, 1H); 6.1 (m 2H); 3 (t, 2H); 2-0.7 (m, 12H).

4a) 2-pentyl-6-aminobenzothiazole hydrochloride

10% Pd/C (0.88 g) is added to 2-pentyl-6-nitrobenzothiazole (10.3 g, 0.041 mol) in methanol (250 ml). The mixture is hydrogenated, the catalyst is filtered off and the filtrate is evaporated. The residue is taken up in methanol, isopropyl ether/HCl is added and the hydrochloride is precipitated. Yield: 9.29 g (89%); Rf (95/5 methylene chloride/methanol): 0.75; IR (KBr): 3465, 3395, 2955, 1505, 1455, 1155, 810 $cm^{-1}$.

4b) 2-pentyl-6-nitrobenzothiazole

2-Pentylbenzothiazole hydrochloride (20.5 g, 0.084 mol) is added, at 0° C., to trifluoromethanesulfonic acid (44.6 ml 0.504 mol) and 100% nitric acid (10.6 ml, 0.215 mol) in methylene chloride (270 ml), and the mixture is stirred at 0° C. for 1.5 hours and at room temperature for one hour. Water (150 ml) is added dropwise and the phases are separated. The organic phase is washed with 0.5M NaHCO₃ and with water. The resulting solution is dried, filtered and concentrated. The solid obtained is recrystallized from petroleum ether. Yield: 10.6 g (50%); Rf (8/2 petroleum ether/ethyl acetate): 0.71; $^1$H-NMR ($d_6$-DMSO) 9.05 (d, 1H); 8.25 (dd, 1H); 8.15 (d, 1H); 3.13 (t, 2H); 1.28-1.36 (m, 4H); 0.85 (t, 3H).

4c) 2-pentylbenzothiazole hydrochloride

PPA (140 g) is added to hexanoic acid (25.06 ml, 0.2 mol) and 2-mercaptoaniline (21.84 ml, 0.2 mol). The mixture is heated at 120° C. for 30 minutes. The resulting mixture is cooled and water (200 ml) is added dropwise, followed by addition of 32% NaOH (pH=10). The resulting mixture is extracted with ethyl acetate and washed with water. The resulting solution is dried and evaporated, the residue is taken up in methanol, isopropyl ether/HCl is added and the hydrochloride is precipitated. Yield: 43.8 g (90%); Rf (8/2 petroleum ether/ethyl acetate): 0.78; m.p.: 106.6-109.0° C.; IR (KBr): 30.75, 2925, 2210, 1884, 1440, 775 $cm^{-1}$.

Example 5

Compound 5

N-(2-phenyl-1H-indol-5-yl)acetamidine

Prepared in a manner similar to that of Example 1. Yield: (63%); Elem. anal. $C_{16}H_{15}N_3$ M.W.: 249.31; theory C, 77.08; H, 6.06; N, 16.85. found C, 76.97; H, 6.29; N, 16.85. IR (KBr): 3434, 3024, 1634, 1597 $cm^{-1}$; $^1$H-NMR ($d_6$-DMSO) 7.8-6.3 (m, 9H); 1.8 (s, 3H).

5a) 2-phenyl-5-amino-1H-indole

Prepared in a manner similar to that of Example 4a. Yield: (83%); Rf (2/1 hexane/ethyl acetate): 0.30; m.p.: 220.2-220.5° C. Elem. anal. $C_{14}H_{12}N_2$; theory C, 80.74; H, 5.81; N, 13.45. found C, 80.55; H, 5.76; N, 13.35. IR (KBr): 3416, 3036, 1622, 1585 $cm^{-1}$.

5b) 2-phenyl-5-nitro-1H-indole

This intermediate is prepared by nitration of 2-phenylindole (6 g, 31 mmol) with NaNO₃ (2.8 g, 33 mmol) in 97% H₂SO₄ (200 mL) at 5° C. Yield: 6.9 g (93%); m.p.: 198.7-200° C. (lit. 201-203° C.; Wayland, E. N. et al. *J.O.C.* 1966, 65).

Example 6

Compound 6

N-(1-methyl-2-phenyl-1H-indol-5-yl)acetamidine

Prepared in a manner similar to that of Example 1. Yield: 68%; Elem. anal. $C_{17}H_{17}N_3$; theory C, 77.54; H, 6.51; N, 15.96. found C, 76.77; H, 6.83; N, 15.65. IR (KBr): 3441, 3013, 1634, 1597 $cm^{-1}$; $^1$H-NMR ($d_6$-DMSO) 7.90-7.20 (m, 6H); 6.90 (d, J=1.5 Hz, 1H) 6.60 (dd, J=8.6 Hz, 1.5 Hz, 1H); 6.40 (s, 1H); 5.90 (bs, 2H, exch. $D_2O$); 3.75 (s, 3H); 1.8 (s, 3H).

6a) 5-amino-2-phenyl-1-methylindole

Prepared in a manner similar to that of Example 4a. Yield: 86%; Rf (2/1 hexane/ethyl acetate): 0.30; m.p.: 107.5-110.5° C. IR (KBr): 3388, 3020, 1622, 1472 $cm^{-1}$.

6b) 2-phenyl-1-methyl-5-nitroindole

Sodium hydride (1.1 g, 29.0 mmol) is added to 2-phenyl-5-nitro-1H-indole (Example 5b, 6.5 g, 26.0 mmol) in 100 mL of DMF. The mixture is stirred at room temperature for 1 hour. MeI (1.62 mL, 26.0 mmol) is added dropwise and the mixture is stirred at room temperature for 1 hour. The resulting mixture is poured into H₂O/ice and the product is filtered off and washed with H₂O. The solid is recrystallized from hexane and filtered off. Yield: 6.5 g (99.7%); Rf (2/1 hexane/ethyl acetate): 0.60; IR (KBr): 3434, 2923, 1515, 1462 $cm^{-1}$; $^1$H-NMR ($d_6$-DMSO) 8.50 (d, J=1.5 Hz, 1H); 7.90 (dd, J=8.6 Hz, 1.5 Hz, 1H); 7.80-7.30 (m, 6H); 6.75 (s, 1H); 3.75 (s, 3H).

EXAMPLES OF PREPARATION OF COMPOUNDS OF FORMULA (I) ACCORDING TO THE SYNTHETIC ROUTE (b)

Example 7

Compound 5

As an alternative to the method described in Example 5, this product may be prepared as reported below:

N-(2-phenyl-1H-indol-5-yl)acetamidine

Prepared in a manner similar to that of Example 5. Yield: 60%; Elem. anal. $C_{16}H_{15}N_3$; theory C, 77.08; H, 6.06; N, 16.85. found C, 77.17; H, 5.89; N, 16.68. IR (KBr): 3434, 3024, 1634, 1597 $cm^{-1}$; $^1$H-NMR ($d_6$-DMSO) 7.8-6.3 (m, 9H); 1.8 (s, 3H).

7a) 2-phenyl-5-amino-1H-indole

Bromobenzene (0.157 ml, 0.0014 mol) and dichlorobis(triphenylphosphine)palladium (II) (51.3 mg, 0.073 mmol) are added to 2-boronic acid 1-N-BOC-5-(N',N'-bisBOC)aminoindole (0.69 g, 0.0014 mol) in THF (10 ml). The mixture is refluxed for 24 hours, 4N HCl (4 ml) are added and the resulting mixture is heated at 80° C. for 10 hours. The resulting mixture is basified with 4M NaOH (pH=10) and extracted with ethyl acetate. The organic phases are combined, washed with water, dried, filtered and concentrated. The solid obtained is recrystallized from isopropyl ether. Rf (2/1 hexane/ethyl acetate): 0.30; m.p.: 220.2-220.5° C. Elem. anal. $C_{14}H_{12}N_2$ theory C, 80.74; H, 5.81; N, 13.45. found C, 80.55; H, 5.76; N, 13.35. $^1$H-NMR ($d_6$-DMSO) 11.0 (s, 1H, exch. $D_2O$); 7.8 (dd, J=8.6 Hz, 1.5 Hz, 1H); 7.6-7.20 (m, 4H); 7.05 (d, J=8.6 Hz, 1H); 6.8-6.3 (m, 3H); 4.5 (bs, 2H, exch. $D_2O$).

7b) 2-Boronic acid 1-N-BOC-5-(N',N'-bisBOC)aminoindole

Triisopropyl borate (0.8 ml, 0.0035 mol) is added to 1-N-BOC-5-(N',N'-bis-BOC)aminoindole (1 g, 0.0023 mol) in THF (3 ml). The mixture is cooled to −5° C. and 2M lithium diisopropylamide (1.38 ml, 0.0028 mol) is added. The mixture is stirred at room temperature for 3 hours and 1M HCl is added (pH=3). The resulting mixture is extracted with ethyl acetate and the organic phase is washed with water. The resulting solution is dried and concentrated. The solid is recrystallized from isopropyl ether. Yield: 0.56 g (51%); $^1$H-NMR ($d_6$-DMSO) 8.1 (s, 2H); 8.0 (d, 1H) 7.3 (d, 1H); 7.0 (dd, 1H); 6.6 (s, 1H); 1.6 (s, 9H); 1.3 (s, 18H).

7c) 1-N-BOC-5-(N',N'-bisBOC)aminoindole

DMAP (1.66 g, 0.013 mol) and di-tert-butyl dicarbonate (32.6 g, 0.149 mol) are added to 5-aminoindole (9 g, 0.068 mol) in THF (300 ml). The mixture is stirred at room temperature for 48 hours, and further DMAP (0.83 g, 0.007 mol) and di-tert-butyl dicarbonate (14.8 g, 0.068 mol) are added. The resulting mixture is stirred at room temperature for a further 6 days. This mixture is evaporated, and the solid is recrystallized from dilute citric acid and filtered off. The solid is recrystallized from isopropyl ether and filtered off. Yield: 2.04 g; m.p.: 189.6-192.7° C. IR (KBr): 3450, 3140, 1740, 1470, 1160, 1120, 780 cm$^{-1}$; $^1$H-NMR ($d_6$-DMSO) 8 (d, 1H); 7.7 (d, 1H); 7.4 (d, 1H); 7.1 (dd, 1H); 6.7 (d, 1H); 1.6 (s, 9H); 1.3 (s, 18H).

Example 8

Compound 8

N-(2-phenylquinol-6-yl)acetamidine

Prepared in a manner similar to that of Example 1. Yield: 48%; Elem. anal. $C_{17}H_{15}N_3$; theory C, 78.13; H, 5.79; N, 16.08. found C, 77.27; H, 5.91; N, 15.70. IR (KBr): 3345, 3055, 1640, 1600, 1480 cm$^{-1}$; $^1$H-NMR ($d_6$-DMSO) 8.2-8.05 (m, 4H); 7.85 (d, 1H); 7.55-7.7 (m, 2H); 7.4-7.5 (m, 1H); 7.35-7.3 (dd, 1H); 7.25 (bs, 1H); 4.5 (bs, 2H); 2.1 (bs, 3H).

8a) 2-phenyl-6-aminoquinoline

Pd/C (10%; 0.60 g) is added to 2-phenyl-6-nitroquinoline (7 g, 0.028 mol) in THF (300 ml) and methanol (300 ml). The mixture is hydrogenated at room temperature and at 1 atm. The catalyst is filtered off, the filtrate is evaporated and the product is recrystallized from isopropyl ether. Yield: 5.7 g (92%); Rf (9/1 chloroform/methanol): 0.56; IR (KBr): 3455, 3320, 3205, 1625, 1495 cm$^{-1}$.

8b) 2-phenyl-6-nitroquinoline

2-Chloro-6-nitroquinoline (10.5 g, 50.4 mmol) (Byoung S. L. et al. *Heterocycles*. 1998, 48.12, 65), phenylboronic acid (7.4 g, 60.4 mmol), palladium dichloride bis(triphenylphosphine) (0.70 g, 1.01 mmol) and barium hydroxide (38.1 g, 0.121 mol) in 200 ml of anhydrous THF are stirred at 65° C. for 20 hours. The mixture is diluted with water, extracted with $CH_2Cl_2$ and evaporated, and the residue is chromatographed on silica gel (1/1 hexane/ethyl acetate). Yield: 7.8 g (62%); IR (KBr): 3475, 3357, 1592, 1479 cm$^{-1}$.

EXAMPLES OF PREPARATION OF COMPOUNDS OF FORMULA (I) ACCORDING TO THE SYNTHETIC ROUTE (c)

Example 9

Compound 9

N-(2-phenylbenzothiazol-5-yl)acetamidine

Triethylamine (6.9 ml, 0.050 mol) is added to methyl acetamidate hydrochloride (5.44 g, 0.050 mol) in acetonitrile (120 ml). The mixture is stirred for 15 minutes at room temperature and 2-phenyl-5-aminobenzothiazole (1.8 g, 8.56 mmol) is added. The resulting mixture is stirred at room temperature for 72 hours. The mixture is evaporated, the residue is taken up in ethyl acetate and washed with sodium hydroxide, and the product is extracted with 0.1M HCl. The acidic aqueous phases are combined, basified with NaOH (pH=10) and extracted with ethyl acetate. The extracts are washed with water, dried and concentrated. The product is recrystallized from isopropyl ether. Yield: 2.0 g (23%); Elem. anal. $C_{15}H_{13}N_3S$; theory C, 67.39; H, 4.90; N, 15.72. found C, 67.38; H, 5.17; N, 15.61. IR (KBr): 3378, 3053, 1650, 1593 cm$^{-1}$; $^1$H-NMR ($d_6$-DMSO) 8.01 (m, 2H); 7.88 (d, 1H); 7.53 (m, 3H); 7.39 (s, 1H); 6.90 (d, 1H); 1.91 (s, 3H).

9a) 2-phenyl-5-aminobenzothiazole

Prepared in a manner similar to that of Example 1a. Yield: 85%; Rf (8/2 petroleum ether/ethyl acetate): 0.30; IR (KBr) 3439, 3316, 3199, 1621 cm$^{-1}$.

9b) 2-phenyl-5-nitrobenzothiazole

PPA (210 g) is added to benzoic acid (12.96 g, 0.104 mol) and sodium 2-amino-4-nitrothiophenoxide (19.98 g, 0.104 mol) (V. L. Guarda, Heterocyclic Comm., 2000, 1.6, 49-54). The mixture is heated at 115-120° C. for 10 minutes, cooled, and water (200 ml) is added dropwise, followed by addition of 32 percent NaOH (pH=5). The product is filtered off and suspended in $NaHCO_3$ ss, filtered off, washed with water and recrystallized from isopropyl ether. Yield: 17.0 g (64%); IR (KBr): 1515, 1341 cm$^{-1}$; $^1$H-NMR ($d_6$-DMSO) 8.77 (d, 1H); 8.39 (d, 1H); 8.25 (dd, 1H); 8.11 (dd, 1H); 7.61 (m, 4H).

Example 10

Compound 10

N-[2-(2-methoxyphenyl)benzothiazol-5-yl]acetamidine

Prepared in a manner similar to that of Example 9. Yield: 67%; Elem. anal. $C_{16}H_{15}N_3OS$; theory C, 64.62; H, 5.08; N, 14.13. found C, 64.71; H, 5.04; N, 14.29. IR (KBr): 3439, 3067, 1641, 1586, $cm^{-1}$; $^1$H-NMR ($d_6$-DMSO) 8.31 (d, 1H); 7.93 (d, 1H); 7.29 (m, 4H); 6.71 (m, 1H); 6.05 (m, 2H); 3.95 (s, 3H).

10a) 2-(2-methoxyphenyl)-5-aminobenzothiazole

Prepared in a manner similar to that of Example 1a. Yield: 51%; Rf (85/25/1/2 chloroform/methanol/aqueous ammonia/water): 0.84; Elem. anal. $C_{14}H_{12}N_2OS$; theory C, 65.60; H, 4.72; N, 10.93. found C, 65.44; H, 4.61; N, 10.97. IR (KBr): 3418, 3302, 3197, 1606, 1428 $cm^{-1}$.

10b) 2-(2-methoxyphenyl)-5-nitrobenzothiazole

Prepared in a manner similar to that of Example 9b. Yield: 59%; Rf (8/2 petroleum ether/ethyl acetate): 0.54; $C_{14}H_{10}N_2O_3S$; M.W.: 286.30.

Example 11

Compound 11

N-[2-benzylbenzothiazol-5-yl]acetamidine

Prepared in a manner similar to that of Example 9. Yield: 43%; Elem. anal. $C_{16}H_{15}N_3S$; theory C, 68.30; H, 5.37; N, 14.93. found C, 67.90; H, 5.75; N, 14.59. IR (KBr): 3320, 3085, 1625, 1105 $cm^{-1}$; $^1$H-NMR ($d_6$-DMSO) 7.8 (m, 1H); 7.3 (m, 6H); 6.8 (m, 1H); 6.0 (m, 2H); 1.9 (m, 3H).

11a) 2-benzyl-5-aminobenzothiazole

Prepared in Example 1a. Yield: 68%; Rf (95:5:0.5 chloroform/methanol/aqueous ammonia): 0.46; IR (KBr): 3410, 3305, 3205, 1595, 1463, 1425 $cm^{-1}$.

11b) 2-benzyl-5-nitrobenzothiazole

Prepared in a manner similar to that of Example 9b. Yield: 69%; Rf (8:2 petroleum ether/ethyl acetate): 0.58; IR (KBr): 1525, 1335, 695 $cm^{-1}$.

Example 12

Compound 12

N-[2-styrylbenzothiazol-5-yl]acetamidine

Prepared in a manner similar to that of Example 9. Yield: 32%; Elem. anal. $C_{17}H_{15}N_3S$; theory C, 69.60; H, 5.15; N, 14.32. found C, 69.89; H, 5.28; N, 14.11. IR (KBr): 3320, 3080, 1625 $cm^{-1}$; $^1$H-NMR ($d_6$-DMSO) 8.0-7.1 (m, 9H); 6.9 (m, 1H); 6.1 (m, 2H) 1.9 (m, 3H).

12a) 2-styryl-5-nitrobenzothiazole

Prepared in a manner similar to that of Example 1a. Yield: 69%; Rf (8/2 petroleum ether/ethyl acetate): 0.54; IR (KBr): 1515, 1335, 740 $cm^{-1}$.

12b) 2-styryl-5-aminobenzothiazole

Prepared in a manner similar to that of Example 9b. Yield: 68%; Rf (95/5/0.5 chloroform/methanol/aqueous ammonia): 0.50; IR (KBr): 3440, 3330, 1605, 1320 $cm^{-1}$.

Example 13

Compound 13

N-[2-(5-aminosulfonyl-2-methoxyphenyl)benzothiazol-5-yl]acetamidine hydrochloride TEA (1.5 ml, 0.008 mol) is added to methyl acetamidate hydrochloride (0.83 g, 0.008 mol) in acetonitrile (20 ml). The mixture is stirred at room temperature for 15 minutes, and 2-(5-aminosulfonyl-2-methoxyphenyl)-5-aminobenzothiazole (1.0 g, 0.003 mol) is added. The mixture is stirred at 35° C. for 96 hours and filtered. The solid is recrystallized from 9/1 THF/methanol. Yield: 0.22 g (18%); Elem. anal. $C_{16}H_{17}N_4O_3S_2Cl$; IR (KBr): 3034, 1678, 1143 $cm^{-1}$; $^1$H-NMR ($d_6$-DMSO) 8.81 (d, 1H); 8.20 (d, 1H); 7.91 (m, 2H); 7.45 (m, 6H); 4.11 (s, 3H); 2.40 (m, 3H).

13a) 2-(5-aminosulfonyl-2-methoxyphenyl)-5-aminobenzothiazole

Chlorosulfonic acid (16 ml, 0.24 mol) and 2-(2-methoxyphenyl)-5-nitrobenzothiazole (13.5 g, 0.047 mol) are stirred together at 0° C. for 15 minutes, the mixture is allowed to warm to room temperature and stirring is continued for one hour. The mixture is poured into ice-water and the product is filtered off and washed with water. The product is added portionwise to a mixture of 32% aqueous ammonia (80 ml) and water (150 ml) at 0° C. This mixture is stirred for 2 hours at 0° C., and is allowed to warm to room temperature, acidified with HCl and filtered. The product is added to a solution of tin dichloride (31.8 g, 0.151 mol) in conc. HCl (43 ml) at 0° C. This mixture is heated at 95° C. for 60 minutes. It is cooled and brought to pH=7.5 with NaOH. The resulting mixture is extracted with chloroform. The extracts are concentrated and the product obtained is recrystallized from isopropyl ether/methanol. Yield: 1.3 g; $^1$H-NMR ($d_6$-DMSO) 8.81 (d, 1H); 7.87 (dd, 1H); 7.64 (d, 1H); 7.35 (m, 4H); 6.65 (dd, 2H); 4.09 (s, 3H).

Example 14

Compound 14

N-[2-(2-pyridyl)benzothiazol-5-yl]acetamidine

Prepared from 2-(2-pyridyl)-5-aminobenzothiazole in a manner similar to that of Example 1. Yield: 2.2 g (59%); Elem. anal. $C_{14}H_{12}N_4S$; theory C, 62.66; H, 4.51; N, 20.88. found C, 61.92; H, 4.55; N, 20.65. IR (KBr): 3390, 3050, 1650, 1590 $cm^{-1}$; $^1$H-NMR ($d_6$-DMSO) 8.7 (d, 1H); 8.3-7.2 (m, 5H); 6.90 (m, 1H); 6.1 (m, 2H); 1.91 (m, 3H).

14a) 2-(2-pyridyl)-5-aminobenzothiazole

PPA (500 g) is added to picolinic acid (24.6 g, 0.2 mol) and sodium 2-amino-4-nitrothiophenoxide (47 g, 0.2 mol). The mixture is heated at 120-130° C. for 6 hours. The resulting mixture is cooled and NaOH is added dropwise (pH=10). The product is filtered off and washed with water. The 2-(2-pyridyl)-5-nitrobenzothiazole is recrystallized from 9/1 isopropyl ether/methanol and is added to a solution of tin dichloride (61.6 g, 0.273 mol) in conc. HCl (50 ml) at 0° C. This mixture is heated at 95° C. for 120 minutes. It is cooled and NaOH is added dropwise (pH=10). The resulting mixture is extracted with chloroform and the combined organic phases are extracted with 0.5M HCl. The acidic aqueous phases are combined, basified with NaOH (pH=10) and extracted with ethyl acetate. The extracts are washed with water and evaporated. The solid obtained is recrystallized from isopropyl ether. Yield: 3.6 g; Rf (9/1 chloroform/methanol): 0.45; IR (KBr): 3400, 3325, 3215, 1590, 1430, 1320, 780 cm$^{-1}$.

Example 15

Compound 15

N-[2-(4-methoxyphenyl)benzothiazol-5-yl]acetamidine

Prepared in a manner similar to that of Example 9. Yield: 59%; Elem. anal. $C_{16}H_{15}N_3OS$; theory C, 64.62; H, 5.08; N, 14.13. found C, 64.46; H, 5.10; N, 13.99. IR (KBr): 3435, 3330, 3200, 1640, 1245 cm$^{-1}$; $^1$H-NMR ($d_6$-DMSO) 8.0 (m, 3H); 7.1 (m, 4H); 6.1 (m, 2H); 3.8 (s, 3H); 1.9 (m, 3H).

15a) 2-(4-methoxyphenyl)-5-aminobenzothiazole

Iron powder (45.9 g, 0.822 mol), water (70 ml) and 37% hydrochloric acid (1.6 ml, 0.019 mol) are added to 2-(4-methoxyphenyl)-5-nitrobenzothiazole (10.95 g, 0.038 mol) in ethanol (300 ml). The mixture is heated at 80° C. for one hour. The resulting mixture is filtered and evaporated, and the residue is taken up in ethyl acetate and basified with NaOH (pH=11). The organic phase is filtered and washed with water. The resulting solution is evaporated and the product obtained is recrystallized from isopropyl ether. Yield: (61%); Rf (9/1 chloroform/methanol): 0.60; Elem. anal. $C_{14}H_{12}N_2OS$; theory C, 65.60; H, 4.72; N, 10.93. found C, 65.44; H, 4.87; N, 10.37. IR (KBr): 3440, 3320, 1600, 1465, 1245, 1170 cm$^{-1}$.

15b) 2-(4-methoxyphenyl)-5-nitrobenzothiazole

Prepared in a manner similar to that of Example 9b. Yield: 45%; Rf (8/2 petroleum ether/ethyl acetate): 0.45; IR (KBr): 1600, 1515, 1485, 1255 cm$^{-1}$.

Example 16

Compound 16

N-[2-(2,4-dimethoxyphenyl)benzothiazol-5-yl]acetamidine

Prepared in a manner similar to that of Example 9. Yield: 40%; Elem. anal. $C_{17}H_{17}N_3O_2S$; theory C, 62.36; H, 5.23; N, 12.83. found C, 62.19; H, 5.13; N, 12.71. IR (KBr): 3420, 3310, 1645, 1440, 1280 cm$^{-1}$; $^1$H-NMR ($d_6$-DMSO) 8.2 (m, 1H); 7.8 (m, 1H); 6.9 (m, 4H); 6.1 (m, 2H); 4.0 (s, 3H); 3.9 (s, 3H); 1.9 (m, 3H).

16a) 2-(2,4-dimethoxyphenyl)-5-aminobenzothiazole

Prepared in a manner similar to that of Example 15a. Yield: 44%; Rf (9/1 chloroform/methanol): 0.67; Elem. anal. $C_{15}H_{15}N_2O_2S$; theory C, 62.70; H, 5.26; N, 9.75. found C, 62.87; H, 4.79; N, 9.16. IR (KBr): 3440, 3285, 3190, 1605, 1500, 1285, 1025 cm$^{-1}$.

16b) 2-(2,4-dimethoxyphenyl)-5-nitrobenzothiazole

Prepared in a manner similar to that described in Example 9b. Yield: 54%; Rf (6/4 toluene/ethyl acetate): 0.77; IR (KBr) 3435, 2935, 1605, 1510, 1285, 816 cm$^{-1}$.

Example 17

Compound 17

N-[2-(3-methoxyphenyl)benzothiazol-5-yl]acetamidine

Prepared in a manner similar to that of Example 9. Yield: 19%; Elem. anal. $C_{16}H_{15}N_3OS$; theory C, 64.62; H, 5.08; N, 14.13. found C, 64.49; H, 5.62; N, 12.80. IR (KBr): 3310, 3065, 1594, 1435, 1270 cm$^{-1}$; $^1$H-NMR ($d_6$-DMSO) 7.9 (m, 1H); 7.3 (m, 6H); 6.1 (m, 2H); 3.8 (s, 3H); 1.9 (m, 3H).

17a) 2-(3-methoxyphenyl)-5-aminobenzothiazole

Prepared in a manner similar to that of Example 15a. Yield: 70%; Rf (9/1 chloroform/methanol): 0.70; IR (KBr): 3430, 3315, 3205, 1600, 1270, 820 cm$^{-1}$.

17b) 2-(3-methoxy-phenyl)-5-nitrobenzothiazole

Prepared in a manner similar to that described in Example 9b. Yield: 22%; Rf (8/2 petroleum ether/ethyl acetate): 0.57; IR (KBr): 1673, 1515, 1340, 740 cm$^{-1}$.

Example 18

Compound 18

N-[2-(2-methylphenyl)benzothiazol-5-yl]acetamidine

Prepared in a manner similar to that of Example 9. Yield: 33%; Elem. anal. $C_{16}H_{15}N_3S$; theory C, 68.30; H, 5.37; N, 14.93. found C, 68.10; H, 5.32; N, 1.74. IR (KBr): 3310, 3065, 1594, 1435, 1270 cm$^{-1}$; $^1$H-NMR ($d_6$-DMSO) 7.9 (m, 2H); 7.5 (m, 4H); 6.9 (m, 1H); 2.6 (s, 3H); 1.9 (m, 3H).

18a) 2-(2-methylphenyl)-5-aminobenzothiazole hydrochloride

Prepared in a manner similar to that of Example 15a. Yield: 65%; Rf (9/1 chloroform/methanol): 0.72; IR (KBr): 2860, 2610, 1530, 1450, 755 cm$^{-1}$.

18b) 2-(2-methylphenyl)-5-nitrobenzothiazole

Prepared in a manner similar to that of Example 9b. Yield: 48%; Rf (8/2 petroleum ether/ethyl acetate): 0.67; IR (KBr) 1678, 1515, 1340 cm$^{-1}$.

Example 19

Compound 19

N-[2-(4-fluorophenyl)benzimidazol-5-yl]acetamidine dihydrochloride

Prepared in a manner similar to that of Example 9. Yield: 36%; Elem. anal. $C_{15}H_{15}Cl_2FN_4$; theory C, 52.80; H, 4.43; N, 16.42. found C, 52.43; H, 4.71; N, 16.01. IR (KBr): 3042, 1677, 1616, 1441, 1233 cm$^{-1}$; $^1$H-NMR (d$_6$-DMSO) 11.40 (s, 1H); 9.45 (s, 1H); 8.36 (m, 3H); 7.29 (m, 6H); 2.25 (m, 3H).

19a) 2-(4-fluorophenyl)-5-aminobenzimidazole dihydrochloride

Prepared in a manner similar to that of Example 4a. Yield: 74%; Rf (95/5/0.5 chloroform/methanol/aqueous ammonia): 0.33; IR (KBr): 2810, 1612, 1505, cm$^{-1}$; $^1$H-NMR (d$_6$-DMSO) 10.42 (m, 5H); 8.38 (m, 2H); 7.62 (m, 7H).

19b) 2-(4-fluorophenyl)-5-nitrobenzimidazole

Prepared from 4-nitrophenylenediamine and 4-fluorobenzoic acid, in a manner similar to that of Example 9b. Yield: 76%; Rf (7/3 toluene/ethyl acetate): 0.54; IR (KBr): 3312, 1601, 1498, 1333 cm$^{-1}$.

Example 20

Compound 20

N-[2-(4-chlorophenyl)benzimidazol-5-yl]acetamidine

Prepared in a manner similar to that of Example 1. Yield: 54%; C$_{15}$H$_{13}$ClN$_4$; IR (KBr) 3425, 3300, 3145, 1637, 1475 cm$^{-1}$; $^1$H-NMR (d$_6$-DMSO) 8-8.2 (m, 3H); 7.3-7.7 (m, 4H); 6.9-6.5 (m, 2H); 1.8 (s, 3H).

20a) 2-(4-chlorophenyl)-5-aminobenzimidazole hydrochloride

Prepared in a manner similar to that of Example 4a. Yield: 94%; Rf (95/5/0.5 chloroform/methanol/aqueous ammonia): 0.22; IR (KBr): 3330, 1635, 1470, 1090, 825 cm$^{-1}$.

20b) 2-(4-chlorophenyl)-5-nitrobenzimidazole

Prepared from 4-chlorobenzoic acid (17.83 g, 0.114 mol) and 2-amino-5-nitroaniline (18 g, 0.114 mol), in a manner similar to that of Example 9b. Yield: 87%; Rf (6/4 toluene/ethyl acetate): 0.61; m.p.: 302.5-305° C.

Example 21

Compound 21

N-(2-phenyl-3H-benzimidazol-5-yl)acetamidine hydrochloride

Prepared in a manner similar to that of Example 1. Yield: 39%; Elem. anal. C$_{15}$H$_{15}$ClN$_4$; theory C, 62.83; H, 5.27; N, 19.54. found C, 61.59; H, 6.09; N, 19.02. IR (KBr): 3347, 3190, 1638, 1590, 1460 cm$^{-1}$; $^1$H-NMR (d$_6$-DMSO) 8.1-8.4 (m, 2H); 7.3-7.8 (m, 4H); 6.9 (d, J=1.5 Hz, 1H); 6.6 (dd, J=8.6 Hz, 1.5 Hz, 1H); 1.8 (s, 3H).

21a) 2-phenyl-5-aminobenzimidazole

Prepared in a manner similar to that of Example 4a. Yield: 4.2 g (74%); Rf (9/1 chloroform/methanol): 0.20; Elem. anal. C$_{13}$H$_{11}$N$_3$; theory C, 74.62; H, 5.29; N, 20.08. found C, 73.95; H, 5.26; N, 19.92.

21b) 2-phenyl-5-nitrobenzimidazole

Prepared from 4-nitrophenylenediamine and benzoic acid in a manner similar to that of Example 9b. Yield: 70%; Rf (9/1 chloroform/methanol): 0.45; IR (KBr): 3290, 1500, 1330, 1290 cm$^{-1}$.

Example 22

Compound 22

N-(2-pentyl-3H-benzimidazol-5-yl)acetamidine dihydrochloride

Prepared in a manner similar to that of Example 1. Yield: 61%; Elem. anal. C$_{14}$H$_{22}$Cl$_2$N$_4$; theory C, 53.01; H, 6.99; N, 17.66. found C, 53.20; H, 7.00; N, 17.63. IR (KBr): 3300, 2866, 1671, 1609 cm$^{-1}$; $^1$H-NMR (d$_6$-DMSO) 11.7 (bs, 1H); 9.8 (bs, 1H); 8.6 (bs, 1H); 7.8 (d, J=8.6 Hz, 1H); 7.7 (d, J=1.5 Hz, 1H); 7.4 (dd, J=8.6 Hz, 1.5 Hz, 1H); 3.14 (t, 2H); 2.41 (s, 3H); 1.90 (m, 2H); 1.57-1.05 (m, 4H); 0.87 (t, 3H).

22a) 2-pentyl-5-amino-3H-benzimidazole

Prepared in a manner similar to that of Example 4a. Yield: 98%.

22b) 2-pentyl-5-nitro-3H-benzimidazole

Prepared from 4-nitrophenylenediamine in a manner similar to that of Example 4c. Yield: 78%; Rf (9/1 chloroform/methanol): 0.70; $^1$H-NMR (CDCl$_3$) 10.2 (bs, 1H); 8.4 (d, J=1.5 Hz, 1H); 8.1 (dd, J=8.6 Hz, 1.53 Hz, 1H); 7.5 (d, J=8.6 Hz, 1H); 3.0 (t, 2H); 1.90 (m, 2H); 1.6-1.1 (m, 4H); 0.87 (t, 3H).

Example 23

Compound 23

N-[2-(pyrrol-2-yl)-3H-benzimidazol-5-yl]acetamidine dihydrochloride

1N NaOH (pH=10) is added to N-[2-(pyrrol-2-yl)-3H-benzimidazol-5-yl]acetamidine hydrobromide (Example 24) (2.2 g, 0.007 mol) in water (30 ml). The precipitate is filtered off and recrystallized from isopropyl ether. The solid is taken up in methanol and the dihydrochloride is precipitated from isopropyl ether/HCl. Yield: 1.7 g (79%); Elem. anal. C$_{13}$H$_{15}$Cl$_2$N$_5$; theory C, 50.01; H, 4.84; N, 22.43. found C, 50.05; H, 4.79; N, 22.17. IR (KBr): 3044, 1674, 1620 cm$^{-1}$.

Example 24

Compound 24

N-[2-(pyrrol-2-yl)-3H-benzimidazol-5-yl]acetamidine hydrobromide

2-Naphthylmethyl thioacetamidate hydrobromide (3.3 g, 0.011 mol) is added, at room temperature and with stirring, to 2-(pyrrol-2-yl)-5-amino-1H-benzimidazole (2.2 g, 0.011 mol) in ethanol (30 ml). The mixture is stirred for 18 hours at room temperature and filtered, and the solid is recrystallized from isopropyl ether. Yield: 3.0 g (85%); C$_{13}$H$_{13}$N$_5$.HBr; m.p.: 197-199° C.; IR (KBr): 3053, 1675, 1629, 1601, 1508 cm$^{-1}$; $^1$H-NMR (d$_6$-DMSO) 11.6 (s, 1H); 11.1 (s, 1H); 9.3 (s, 1H); 8.4 (s, 1H); 7.5 (d, 1H); 7.4 (d, 1H); 7.0 (m, 2H); 6.2 (m, 2H); 2.4 (s, 3H).

24a) 2-(pyrrol-2-yl)-5-amino-1H-benzimidazole

Prepared in a manner similar to that of Example 4a. Yield: 38%; Rf (85/25/2/1 chloroform/methanol/water/aqueous ammonia): 0.67; IR (KBr): 3367, 1630 cm$^{-1}$; $^1$H-NMR (d$_6$-DMSO) 11.5 (m, 1H); 7.2 (d, 1H); 6.6-6.9 (m, 3H); 6.5 (dd, 2H); 6.1 (m, 1H).

24b) 2-(pyrrol-2-yl)-5-nitro-1H-benzimidazole

Pyrrolyl-2-carboxaldehyde (10.6 g, 0.104 mol) is added to 2-amino-4-nitroaniline (14 g, 0.090 mol) in DMF (400 ml), and the mixture is heated at 110° C. for 60 hours, cooled and concentrated. The solid is recrystallized from water and then from isopropyl ether. Yield: 15.5 g (71); IR (KBr): 3100, 1596, 1506, 1327 cm$^{-1}$; $^1$H-NMR (d$_6$-DMSO) 8.2 (m, 1H); 8.0 (m, 1H); 7.5-7.7 (m, 1H); 6.9 (m, 3H); 6.2 (m, 2H).

Example 25

Compound 25

Methyl 4-(5-acetimidoylamino-1H-benzimidazol-2-yl)benzoate hydrochloride

Prepared in a manner similar to that of Example 1. Yield: 27%; IR (KBr): 3447, 3050, 1717, 1610, 1277 cm$^{-1}$; $^1$H-NMR (d$_6$-DMSO) 11.61 (s, 1H); 9.54 (s, 1H); 8.53 (d, 2H); 8.12 (d, 2H); 7.78 (m, 3H); 7.25 (dd, 2H); 6.64 (m, 3H); 3.81 (s, 3H); 2.34 (s, 3H).

25a) Methyl 4-(5-amino-1H-benzimidazol-2-yl)benzoate

Prepared in a manner similar to that of Example 4a. Yield: 57%; Rf (9/1 chloroform/methanol): 0.33; Elem. anal. C$_{15}$H$_{13}$N$_3$O$_2$; theory C, 67.40; H, 4.90; N, 15.72. found C, 66.24; H, 4.89; N, 14.54. IR (KBr): 3311, 1689, 1611, 1282, 1111 cm$^{-1}$.

25b) Methyl 4-(5-nitro-1H-benzimidazol-2-yl)benzo-ate

Sodium bisulfite (7.0 g, 0.036 mol) in water (70 ml) is added to 4-carboxybenzaldehyde (11.0 g, 0.071 mol) in ethanol (70 ml). The mixture is stirred at room temperature for 15 minutes, the solid is filtered off, the filtrate is coevaporated with toluene and a solution of 2-amino-5-nitroaniline (11.1 g, 0.071 mol) in DMF (250 ml) is added. This mixture is refluxed for 3 hours and concentrated, and the product is recrystallized from dilute HCl, filtered off and washed with water. The solid is suspended in methanol (300 ml) and HCl gas is bubbled through at 5-15° C. for 3 hours. The mixture is allowed to warm to room temperature and is then refluxed for 3 hours. The solution is concentrated to 1/3 of its volume and cooled to +5° C., and the precipitate is filtered off and recrystallized from NaHCO$_3$ and finally from 3/1 isopropyl ether/hexane. Yield: 15 g (71%); IR (KBr): 3570, 3472, 3112, 1707, 1301 cm$^{-1}$; $^1$H-NMR (d$_6$-DMSO) 7.7-8.5 (m, 7H); 5.9 (m, 1H); 3.88 (s, 3H).

Example 26

Compound 26

4-(5-acetimidoylamino-1H-benzimidazol-2-yl)benzoic acid

Prepared in a manner similar to that of Example 1. Yield: 67%; Elem. anal. C$_{16}$H$_{14}$N$_4$O$_2$; theory C, 65.30; H, 4.79; N, 19.04. found C, 63.31; H, 5.37; N, 17.19. IR (KBr): 3220, 1590, 1544, 1378 cm$^{-1}$.

26a) 4-(5-amino-1H-benzimidazol-2-yl)benzoic acid

Prepared in a manner similar to that of Example 4a. Yield: 83%; Rf (4/4/2 chloroform/methanol/aqueous ammonia): 0.70; IR (KBr): 3117, 1604, 1540, 1397 cm$^{-1}$.

26b) 4-(5-nitro-1H-benzimidazol-2-yl)benzoic acid

2M NaOH (75 ml) is added, at 0° C., to methyl 4-(5-nitro-1H-benzimidazol-2-yl)benzoate (15 g, 0.050 mol) (Example 26) in methanol (250 ml). The mixture is stirred at room temperature for 20 hours and evaporated, and the residue is taken up in water and acidified with HCl (pH=6). The resulting mixture is stirred for 16 hours at 0° C., and the product is filtered off, washed with water and recrystallized from 9/1 methanol/isopropyl ether. Yield: 10 g (70%); IR (KBr): 3357, 1675, 1602, 1537, 1377, 1320 cm$^{-1}$; $^1$H-NMR (d$_6$-DMSO) 7.5-8.6 (m, 7H).

Example 27

Compound 27

N-(2-phenylquinazolin-6-yl)acetamidine dihydrochloride

Isopropyl ether/HCl is added to 2-phenyl-6-(N-acetamidino)quinazoline (0.9 mg, 0.0.034 mol) in methanol (5 ml) at 0° C. The product is filtered off and recrystallized from isopropyl ether/isopropyl alcohol. Yield: 0.8 g (20%); Elem. anal. C$_{16}$H$_{16}$Cl$_2$N$_4$; theory C, 57.32; H, 4.81; N, 16.71. found C, 56.38; H, 6.05; N, 15.29. IR (KBr): 3453, 3095, 1658, 1600, 1553, 1343 cm$^{-1}$; $^1$H-NMR (d$_6$-DMSO) 11.81 (s, 1H); 9.74 (s, 2H); 8.83 (m, 1H); 8.48 (m, 2H); 8.12 (m, 2H); 7.83 (d, 1H); 7.34 (m, 4H); 2.34 (s, 3H).

27b) N-(2-phenylquinazolin-6-yl)acetamidine

Prepared in a manner similar to that of Example 9. Yield: 20%; m.p.: 162-164° C. Elem. anal. C$_{15}$H$_{13}$N$_3$S; theory C, 73.26; H, 5.38; N, 21.36. found C, 72.65; H, 5.46; N, 21.09. IR (KBr): 3453, 3095, 1658, 1600, 1553, 1343 cm$^{-1}$; $^1$H-NMR (d$_6$-DMSO) 9.41 (s, 1H); 8.48 (m, 2H); 7.83 (d, 1H); 7.34 (m, 6H); 6.30 (m, 1H) 1.85 (s, 3H).

27c) 2-phenyl-6-aminoquinazoline

Prepared in a manner similar to that of Example 4a. Yield: 74%; Elem. anal. C$_{14}$H$_{11}$N$_3$; theory C, 76.00; H, 5.01; N, 18.99. found C, 75.85; H, 5.12; N, 18.58. IR (KBr): 3455, 3315, 1622, 1494, 1385, 1242 cm$^{-1}$; $^1$H-NMR (d$_6$-DMSO) 9.21 (s, 1H); 8.45 (m, 1H); 7.50 (m, 5H); 6.85 (d, 1H); 5.88 (s, 2H).

27d) 2-phenyl-6-nitroquinazoline

2-Phenyl-6-nitro-3,4-dihydroquinazoline (27 g, 0.106 mol) and chloranil (32.4 g, 0.13 mol) in toluene (450 ml) are refluxed for 60 minutes. The mixture is cooled to room temperature, and the precipitate is filtered off and washed with toluene (350 ml). The filtrate is suspended in 0.5N NaOH (400 ml) and the aqueous phase is extracted with dichloromethane (100 ml). The combined organic phases are washed with water and concentrated. The solid is recrystallized from hexane. Yield: 8.8 g (34%); Rf (8/2 petroleum ether/ethyl acetate): 0.71; $^1$H-NMR (d$_6$-DMSO) 9.91 (s, 1H); 9.18 (d, 1H); 8.61 (m, 3H); 8.24 (d, 1H); 7.55 (m, 3H).

27e) 2-phenyl-6-nitro-3,4-dihydroquinazoline

N-Benzoyl-2-amino-5-nitrobenzylamine (33 g, 0.12 mol) and phosphoryl chloride (150 ml) are refluxed for 3 hours. The mixture is concentrated and water is added, followed by addition of aqueous ammonia (pH>10). The product is filtered off and recrystallized from water, and then from 2/1 isopropyl ether/hexane. Yield: 27.6 g (89%); IR (KBr): 3387, 3198, 1599, 1512, 1341 $cm^{-1}$; $^1$H-NMR ($d_6$-DMSO) 7.95 (m, 4H); 7.30 (m, 4H); 7.01 (m, 1H); 4.71 (s, 2H).

27f) N-benzoyl-2-amino-5-nitrobenzylamine

Triethylamine (116 ml, 0.835 mol) and DMAP (2.0 g, 0.016 mol) are added to 2-amino-5-nitrobenzonitrile (68 g, 0.33 mol) in dichloromethane (1 litre). The mixture is cooled to +5° C., and benzoyl chloride (38.8 ml, 0.33 mol) in dichloromethane (50 ml) is added. The resulting mixture is stirred for 2 hours and then concentrated. The residue is taken up in 10/1 water/ethanol (550 ml) and the product is filtered off and recrystallized from isopropyl ether. Yield: 88.5 g (97%); IR (KBr): 3375, 3213, 1638, 1547, 1319 $cm^{-1}$; $^1$H-NMR ($d_6$-DMSO) 8.15 (m, 1H); 7.85 (m, 4H); 7.51 (m, 4H); 6.68 (m, 3H); 4.30 (m, 2H).

27g) 2-amino-5-nitrobenzylamine hydrochloride

Borane in THF (400 ml, 0.40 mol) is added dropwise to 2-amino-5-nitrobenzonitrile (60 g, 0.35 mol) in THF (600 ml) at 0° C. The mixture is allowed to warm to room temperature and is stirred for 16 hours. The resulting mixture is cooled to 0° C. and 200 ml of absolute ethanol/HCl are added. The THF is removed and the product is filtered off and recrystallized from isopropyl ether. Yield: 68.8 g (96%); Rf (1:1 methanol/chloroform): 0.15; IR (KBr): 3416, 2980, 1669, 1601, 1474, 1285 $cm^{-1}$.

Example 28

Compound 28

N-(2-phenylbenzofuran-5-yl)acetamidine 2-naphthylmethyl thioacetamidate hydrobromide (13.03 g, 0.044 mol) is added to 2-phenyl-5-aminobenzofuran (9.31 g, 0.044 mol) in ethanol (200 ml). The mixture is stirred at room temperature for 18 hours and is then evaporated, NaOH (pH=10) is added and the resulting mixture is extracted with ethyl acetate. The organic phase is extracted with 0.5M HCl. The acidic aqueous phases are combined, basified with NaOH (pH=10) and extracted with ethyl acetate. The extracts are washed with water. The resulting solution is evaporated and the solid obtained is recrystallized from isopropyl ether. Yield: 7.45 g (68%); Elem. anal. $C_{16}H_{14}N_2O$; theory C, 76.78; H, 5.64; N, 11.19. found C, 76.18; H, 5.56; N, 11.02. IR (KBr): 3445, 3045, 1640, 1605, 1450, 755 $cm^{-1}$; $^1$H-NMR ($d_6$-DMSO) 7.6-8.0 (m, 2H); 7.1-7.6 (m, 6H); 6.9-6.6 (m, 1H); 5.9 (m, 2H); 1.9 (m, 3H).

28a) 2-phenyl-5-aminobenzofuran

Triethylamine (63.4 ml, 0.455 mol) is added to 2-hydroxy-5-nitrobenzylphsophonium bromide (50 g, 0.101 mol) in refluxing toluene (600 ml), followed by addition of benzoyl chloride (16.2 ml, 0.140 mol) in toluene (50 ml). The mixture is refluxed for 3 hours, cooled and stirred at room temperature for 2 hours. The resulting mixture is concentrated and the product is recrystallized from 2/1 isopropyl ether/hexane, and the 2-phenyl-5-nitrobenzofuran is filtered off. This product is hydrogenated in THF (300 ml) and methanol (150 ml), with Pd/C (10%; 3.2 g). The catalyst is filtered off and the filtrate is concentrated. The residue is taken up in isopropanol/MeOH/HCl, and the hydrochloride is precipitated. It is suspended in 1M NaOH and extracted with ethyl acetate. The extracts are washed with water and concentrated. The solid is recrystallized from isopropyl ether. Yield: 9.8 g (32%); Elem. anal. $C_{14}H_{11}NO$; theory C, 80.36; H, 5.30; N, 6.70. found C, 79.78; H, 5.16; N, 6.87. IR (KBr): 3400, 3325, 1595, 1465 $cm^{-1}$.

Example 29

Compound 29

N-(2-phenylbenzoxazol-5-yl)acetamidine

Prepared in a manner similar to that of Example 9. Yield: 29%; Elem. anal. $C_{15}H_{13}N_3O$; theory C, 71.70; H, 5.21; N, 16.72. found C, 71.48; H, 4.64; N, 16.71. IR (KBr): 3360, 3140, 1655, 1180, 700 $cm^{-1}$; $^1$H-NMR ($d_6$-DMSO) 8-8.2 (m, 2H); 7.4-7.8 (m, 5H); 6.9 (dd, 1H); 5.9-6.3 (broad s, 2H); 1.8 (m, 3H).

29a) 2-phenyl-5-aminobenzoxazole

Prepared in a manner similar to that of Example 4b. Yield: 83%; Rf (9/1 chloroform/methanol): 0.52; m.p.: 155.3-156.7° C. Elem. anal. $C_{13}H_{10}N_2O$; theory C, 74.27; H, 4.79; N, 13.32. found C, 73.48; H, 4.85; N, 13.12. IR (KBr): 3435, 3320, 1545, 1480, 1180, 695 $cm^{-1}$.

29b) 2-phenyl-5-nitrobenzoxazole

Prepared from 2-amino-4-nitrophenol and benzoic acid, in a manner similar to that of Example 9b. Yield: 85%; Rf (9/1 chloroform/methanol): 0.92; Elem. anal. $C_{13}H_8N_2O_3$; theory C, 65.00; H, 3.35; N, 11.66. found C, 64.54; H, 3.35; N, 11.85. IR (KBr): 1615, 1530, 1345 $cm^{-1}$.

Example 30

Compound 30

N-[2-(4-chlorophenyl)benzoxazol-5-yl]acetamidine

Prepared in a manner similar to that of Example 28. Yield: 29%; Rf (5/2/2 butanol/acetic acid/water): 0.58; Elem. anal. $C_{15}H_{12}ClN_3O$; theory C, 62.77; H, 4.25; N, 14.77. found C, 63.05; H, 4.23; N, 14.70. m.p.: 183.6-185.1° C. IR (KBr): 3455, 3295, 3145, 1645, 1400, 835 $cm^{-1}$; $^1$H-NMR ($d_6$-DMSO) 8.1 (m, 2H); 7.6 (m, 3H); 7.1 (m, 1H); 6.9 (m, 1H); 1.9 (broad s, 3H).

30a) 2-(4-chlorophenyl)-5-aminobenzoxazole

Prepared in a manner similar to that of Example 1a. Yield: 44%; IR (KBr): 3430, 3340, 1625, 1595, 1475, 830 $cm^{-1}$.

30b) 2-(4-chlorophenyl)-5-nitrobenzoxazole

Prepared in a manner similar to that of Example 9b. Yield: 28%; Rf (7/3 toluene/chloroform): 0.58; IR (KBr): 3095, 1605, 1525, 1335, 820 $cm^{-1}$.

Example 31

Compound 31

N-[2-(3-trifluromethylphenyl)benzoxazol-5-yl]acetamidine

Prepared in a manner similar to that of Example 28. Yield: 56%; Elem. anal. $C_{16}H_{12}F_3N_3O$; theory C, 60.19; H, 3.79; N, 13.16. found C, 60.44; H, 4.22; N, 13.05. m.p.: 157.9-159.2° C. IR (KBr): 3330, 3105, 1660, 1615, 1280, 1175 cm$^{-1}$; $^1$H-NMR (d$_6$-DMSO) 8.4 (m, 2H); 7.8 (m, 3H); 7.1 (m, 2H); 6.1 (m, 2H); 1.9 (m, 3H).

31a) 2-(3-trifluromethylphenyl)-5-aminobenzoxazole

Prepared in a manner similar to that of Example 4a. Yield: 80%; Rf (9/1 chloroform/methanol): 0.59; IR (KBr): 3435, 3335, 1620, 1340, 1120 cm$^{-1}$.

31b) 2-(3-trifluromethylphenyl)-5-nitrobenzoxazole

3-Trifluoromethylbenzoyl chloride (9.03 g, 0.043 mol) and 2-hydroxy-5-nitroaniline (6.58 g, 0.041 mol) in toluene (200 ml) are refluxed for 48 hours. POCl$_3$ (20 ml) is added, the mixture is refluxed for a further 2 hours and concentrated, and the solid is recrystallized from NaOH (pH=10). The product is filtered off and recrystallized from water and finally from isopropyl ether. Yield: 10.3 g (78%); Rf (8/2 petroleum ether/ethyl acetate): 0.58; IR (KBr): 3085, 1620, 1531, 1425, 1340 cm$^{-1}$.

Example 32

Compound 32

N-[2-(4-trifluromethylphenyl)benzoxazol-5-yl]acetamidine

Prepared in a manner similar to that of Example 28. Yield: 56%; $C_{16}H_{12}F_3N_3O$; IR (KBr): 3455, 3100, 1645, 1610, 1465, 1325, 1115 cm$^{-1}$.

32a) 2-(4-trifluromethylphenyl)-5-aminobenzoxazole

Prepared in a manner similar to that of Example 4a. Yield: 71%; Rf (9/1 chloroform/methanol): 0.50; IR (KBr): 3440, 3355, 1620, 1330, 1105 cm$^{-1}$.

32b) 2-(4-trifluromethylphenyl)-5-nitrobenzoxazole

Prepared in a manner similar to that of Example 31b. Yield: 57%; Rf (8/2 hexane/ethyl acetate): 0.66; IR (KBr): 3105, 1610, 1530, 1345, 1115 cm$^{-1}$.

Example 33

Compound 33

N-[2-(2-fluorophenyl)benzoxazol-5-yl]acetamidine

Prepared in a manner similar to that of Example 28. Yield: 65%; $C_{15}H_{12}FN_3O$; IR (KBr): 3340, 3110, 1655, 1605, 1460, 1395 cm$^{-1}$; $^1$H-NMR (d$_6$-DMSO) 8.4 (m, 2H); 7.8 (m, 3H); 7.1 (m, 2H); 6.1 (m, 2H); 1.9 (m, 3H).

33a) 2-(2-fluorophenyl)-5-aminobenzoxazole

Prepared in a manner similar to that of Example 4a. Yield: 76%; Rf (9/1 chloroform/methanol): 0.61; IR (KBr): 3430, 3325, 1585, 1480, 1445 cm$^{-1}$.

33b) 2-(2-fluorophenyl)-5-nitrobenzoxazole

Prepared in a manner similar to that of Example 31b. Yield: 33%; Rf (8/2 hexane/ethyl acetate): 0.48; IR (KBr): 3095, 1615, 1525, 1485, 1340 cm$^{-1}$.

Example 34

Compound 34

N-[2-(3,4-dichlorophenyl)benzoxazol-5-yl]acetamidine

Prepared in a manner similar to that of Example 28. Yield: 75%; Elem. anal. $C_{15}H_{11}Cl_2N_3O$; theory C, 56.27; H, 3.46; N, 13.12. found C, 56.01; H, 3.58; N, 13.22. IR (KBr): 3449, 3084, 1644, 1460 cm$^{-1}$; $^1$H-NMR (d$_6$-DMSO) 8.3 (d, 2H); 8.1 (dd, 1H); 7.5-7.9 (m, 4H); 7.1 (m, 1H); 6.9 (m, 1H); 1.9 (m, 3H).

34a) 2-(3,4-dichlorophenyl)-5-aminobenzoxazole

Prepared in a manner similar to that of Example 1a. Yield: 55%; Rf (7/3 toluene/ethyl acetate): 0.37; Elem. anal. $C_{13}H_8Cl_2N_2O$; theory C, 55.94; H, 2.89; N, 10.04. found C, 55.55; H, 3.08; N, 9.82. IR (KBr): 3400, 3324, 3211, 1626, 1457 cm$^{-1}$.

34b) 2-(3,4-dichlorophenyl)-5-nitrobenzoxazole 3,4-Dichlorobenzoyl chloride (4.6 g, 0.022 mol) is added to 2-amino-4-nitrophenol (3.4 g, 0.022 mol) in toluene (250 ml) and the mixture is refluxed for 24 hours. para-Toluenesulfonic acid (1.0 g) is added, the mixture is refluxed for 24 hours and cooled, and the product is filtered off. It is recrystallized from isopropyl ether. Yield: 6.8 g; IR (KBr): 3100, 1531, 1350 cm$^{-1}$.

Example 35

Compound 35

N-[2-(3,4-dichlorophenyl)benzimidazol-5-yl]acetamidine

Prepared in a manner similar to that of Example 28. Yield: 37%; Elem. anal. $C_{15}H_{12}Cl_2N_4$; theory C, 56.44; H, 3.79; N, 17.55. found C, 55.84; H, 4.58; N, 16.59. IR (KBr): 3375, 3300, 3170, 1630, 1450, 1395 cm$^{-1}$; $^1$H-NMR (d$_6$-DMSO) 8.3 (d, 1H); 8.1 (dd, 1H); 7.7 (m, 1H); 7.4 (m, 1H); 6.9 (m, 1H); 6.7 (dd, 1H); 1.9 (broad s, 3H).

35a) 2-(3,4-dichlorophenyl)-5-aminobenzimidazole

Prepared in a manner similar to that of Example 1a. Yield: 44%; Rf (95/5/0.5 chloroform/methanol/aqueous ammonia): 0.16; IR (KBr): 1630, 1425, 1130 cm$^{-1}$.

35b) 2-(3,4-dichlorophenyl)-5-nitrobenzimidazole

Prepared from 4-nitro-2-aminophenol and 3,4-dichlorobenzoic acid, in a manner similar to that of Example 9b.

Yield: 28%; Rf (7/3 toluene/ethyl acetate): 0.53; IR (KBr): 3290, 1495, 1440, 1335 cm$^{-1}$.

Example 36

Compound 36

N-[2-(3-trifluoromethylphenyl)benzimidazole-5-yl]acetamidine hydrobromide

Prepared in a manner similar to that of Example 24. Yield: 51%; Elem. anal. $C_{16}H_{14}BrF_3N_4$; theory C, 48.14; H, 3.53; N, 14.03. found C, 48.04; H, 3.85; N, 13.82. IR (KBr): 3040, 1680, 1620, 1410, 1320 cm$^{-1}$; $^1$H-NMR (d$_6$-DMSO) 8.5 (m, 2H); 7.7 (m, 4H) 7.1 (m, 1H); 2.4 (broad s, 3H).

36a) 2-(3-trifluoromethylphenyl)-5-aminobenzimidazole

Prepared in a manner similar to that of Example 4a. Yield: 80%; Rf (9/1 chloroform/methanol): 0.25.

36b) 2-(3-trifluoromethylphenyl)-5-nitrobenzimidazole

Prepared in a manner similar to that of Example 31b. Yield: 41%; Rf (8/2 toluene/ethyl acetate): 0.47; IR (KBr): 3105, 1515, 1325, 1170, 1120 cm$^{-1}$.

Example 37

Compound 37

2-[(2-methoxyphenyl)benzimidazol-5-yl]acetamidine

Prepared in a manner similar to that of Example 1. Yield: 18%; Elem. anal. $C_{16}H_{16}N_4O$; theory C, 68.55; H, 5.75; N, 19.99. found C, 67.79; H, 5.65; N, 19.60. IR (KBr): 3440, 3135, 1640, 1460, 1245 cm$^{-1}$; $^1$H-NMR (d$_6$-DMSO) 8.2 (m, 1H); 7.2 (m, 5H) 6.6 (m, 1H); 3.9 (m, 3H); 1.8 (s, 3H).

37a) 2-(2-methoxyphenyl)-5-aminobenzimidazole dihydrochloride

Prepared in a manner similar to that of Example 4a. Yield: 93%; Rf (9/1 chloroform/methanol): 0.45; IR (KBr): 2835, 2610, 1635, 1495, 1455 cm$^{-1}$.

37b) 2-(2-methoxyphenyl)-5-nitrobenzimidazole

Prepared from 4-nitrophenylenediamine and 2-methoxybenzoic acid, in a manner similar to that of Example 9b. Yield: 76%; Rf (6/4 toluene/ethyl acetate): 0.43; IR (KBr): 3005, 1515, 1335, 750 cm$^{-1}$.

Example 38

Compound 38

N-[2-(2-fluorophenyl)benzimidazol-5-yl]acetamidine hydrobromide

Prepared in a manner similar to that of Example 24. Yield: 82%; Elem. Anal. $C_{15}H_{14}FN_4$.HBr; theory C, 51.59; H, 4.04; N, 16.04. found C, 50.79; H, 4.30; N, 15.45. IR (KBr): 3237, 2885, 1684, 1611 cm$^{-1}$.

38a) 2-(2-fluorophenyl)-5-aminobenzimidazole

Prepared in a manner similar to that of Example 4a. Yield: 100%; Rf (9/1 chloroform/methanol): 0.25.

38b) 2-(2-fluorophenyl)-5-nitrobenzimidazole

Prepared from 4-nitrophenylenediamine and 2-fluorobenzoic acid, in a manner similar to that of Example 31b. Yield: 15%; Rf (7/3 toluene/ethyl acetate): 0.55; IR (KBr): 2996, 1625, 1520, 1479, 1340 cm$^{-1}$; $^1$H-NMR (d$_6$-DMSO) 8.5-8.0 (m, 3H); 7.2-7.9 (m, 4H).

Example 39

Compound 39

N-[2-(2-methylphenyl)benzimidazol-5-yl]acetamidine

Prepared in a manner similar to that of Example 28. Yield: 38%; Elem. anal. $C_{16}H_{16}N_4$; theory C, 72.70; H, 6.10; N, 21.20. found C, 71.00; H, 6.45; N, 20.35. IR (KBr): 3454, 3055, 1643, 1393 cm$^{-1}$; $^1$H-NMR (d$_6$-DMSO) 7.7 (m, 1H); 7.5 (m, 7H); 6.9 (m, 1H); 6.7 (dd, 1H); 2.6 (s, 3H); 1.9 (s, 3H).

39a) 2-(2-methylphenyl)-5-aminobenzimidazole

Prepared in a manner similar to that of Example 4a. Yield: 100%; Rf (9/1 chloroform/methanol): 0.31; IR (KBr): 2966, 1630, 1447 cm$^{-1}$; $^1$H-NMR (d$_6$-DMSO) 8.6 (m, 1H); 7.2 (m, 6H); 6.4-6.7 (m, 3H).

39b) 2-(2-methylphenyl)-5-nitrobenzimidazole

2-Methylbenzoyl chloride (4.1 g, 0.027 mol) is added to 2-amino-4-nitroaniline (4 g, 0.025 mol) in toluene (100 ml), and the mixture is refluxed for 24 hours. para-Toluenesulfonic acid (1.0 g) is added, the mixture is refluxed for 36 hours and concentrated, and the residue is taken up in ethyl acetate. The solution is washed with NaHCO$_3$ and then with water. The resulting solution is dried and concentrated, and the solid obtained is recrystallized from isopropyl ether. Yield: 3.1 g (48%); Rf (7/3 toluene/ethyl acetate): 0.58; $^1$H-NMR (d$_6$-DMSO): 8.5 (d, 1H); 8.1 (dd, 1H); 7.7 (m, 2H); 7.4 (m, 3H); 2.6 (s, 3H).

Example 40

Compound 40

N-[2-(pyrrol-2-yl)benzothiazol-5-yl]acetamidine

Prepared in a manner similar to that of Example 1. Yield: 28%; Elem. anal. $C_{13}H_{12}N_4S$; theory C, 60.91; H, 4.72; N, 21.85. found C, 61.20; H, 5.41; N, 20.07. IR (KBr): 3455, 3165, 1655, 1570, 1485 cm$^{-1}$; $^1$H-NMR (d$_6$-DMSO) 11.5 (broad s, 1H); 7.8 (m, 1H); 7.2-6.6 (m, 4H); 6.3-5.8 (m, 3H), 1.8 (m, 3H).

40a) 2-(2-pyrrolyl)-5-aminobenzothiazole

Prepared in a manner similar to that of Example 4a. Yield: 30%; Rf (9/1 chloroform/methanol): 0.44; IR (KBr): 3455, 3360, 3125, 1570, 1460 cm$^{-1}$.

40b) 2-(2-pyrrolyl)-5-nitrobenzothiazole

Prepared from sodium 2-amino-4-nitrothiophenoxide (15 g, 0.078 mol) and pyrrol-2-ylcarboxaldehyde (5.23 g, 0.055 mol) in a manner similar to that of Example 24b. Yield: 3.9 g (29%); Rf (8/2 petroleum ether/ethyl acetate): 0.54; IR (KBr): 1595, 1510, 1480, 1335 cm$^{-1}$.

Example 41

Compound 41

N-[2-phenylbenzothiazol-5-yl]cyclopropylcarboxamidine

Prepared from 2-phenyl-5-aminobenzothiazole (example 9a) and methyl cyclopropylcarboximidate (Patai, The Chemistry of Functional Groups; The Chemistry of Cyano group; pp. 264-266, zvi Rappoport, Wiley & Sons, 1970) in a manner similar to that described in Example 9. Yield: 57%; Elem. anal. C$_{17}$H$_{15}$N$_3$O; theory C, 73.63; H, 5.45; N, 15.15. found C, 72.06; H, 5.29; N, 14.69. IR (KBr): 3401, 1646, 1604, 1469 cm$^{-1}$.

Example 42

Compound 42

N-(2-phenylbenzoxazol-6-yl)acetamidine

Prepared in a manner similar to that of Example 9. Yield: 41%; Elem. anal. C$_{15}$H$_{13}$N$_3$O; theory C, 71.70; H, 5.21; N, 16.72. found C, 71.06; H, 4.91; N, 16.62. IR (KBr): 3360, 3105, 1655, 1606 cm$^{-1}$; $^1$H-NMR (d$_6$-DMSO) 8-8.2 (m, 2H); 7.4-7.8 (m, 5H); 6.9 (dd, 1H); 5.9-6.3 (broad s, 2H); 1.8 (broad s, 3H).

42a) 2-phenyl-6-aminobenzoxazole

Prepared in a manner similar to that of Example 4a. Yield: 74%; Rf (9/1 chloroform/methanol): 0.64; m.p.: 212-214° C. IR (KBr): 3400, 3305, 3205, 1630 cm$^{-1}$ 42b) 2-phenyl-6-nitrobenzoxazole PPA (160 g) is added to benzoic acid (14.26 g, 0.117 mol) and 2-amino-5-nitrophenol (20 g, 0.117 mol). The mixture is heated at 115-120° C. for 30 minutes and cooled, and water (200 ml) is added dropwise, followed by addition of 32% NaOH (pH=10). The product is filtered off, washed with water and filtered off. It is recrystallized from isopropyl ether. Yield: 25 g (90%); Elem. anal. C$_{13}$H$_8$N$_2$O$_3$; theory C, 65.00; H, 3.35; N, 11.66. found C, 64.56; H, 3.22; N, 11.43. IR (KBr): 1551, 1515, 1340 cm$^{-1}$.

Example 43

Compound 43

N-[1-methyl-2-(2-methoxyphenyl)benzimidazol-5-yl]acetamidine dihydrochloride

Prepared in a manner similar to that of Example 28. Yield: 78%; Elem. anal. C$_{17}$H$_{20}$Cl$_2$N$_4$O; theory C, 55.59; H, 5.49; N, 15.25. found C, 54.36; H, 6.05; N, 14.86. IR (KBr): 3450, 3020, 1605, 1490, 1260 cm$^{-1}$; $^1$H-NMR (d$_6$-DMSO) 12.04 (broad s, 1H); 9.78 (broad s, 1H); 8.65 (broad s, 1H); 8.12 (d, 1H); 7.85 (s, 1H); 7.77 (dt, 1H); 7.71 (dd, 1H); 7.52 (dd, 1H); 7.39 (d, 1H); 7.27 (t, 1H); 3.90 (s, 3H); 3.86 (s, 3H); 2.43 (s, 3H).

43a) 1-methyl-2-(2-methoxyphenyl)-5-aminobenzimidazole and 1-methyl-2-(2-methoxyphenyl)-6-aminobenzimidazole Prepared in a manner similar to that of Example 4a. The amines of the two isomers are separated by flash chromatography on a column of silica gel (ethyl acetate).

1-methyl-2-(2-methoxyphenyl)-6-aminobenzimidazole

Yield: 2.21 g; Rf (95/5/0.5 chloroform/methanol/aqueous ammonia): 0.33; Elem. anal. C$_{15}$H$_{15}$N$_3$O; theory C, 71.12; H, 5.97; N, 16.59. found C, 69.71; H, 6.10; N, 15.29. IR (KBr): 3230, 3200, 2935, 1625, 1460, 1245 cm$^{-1}$; $^1$H-NMR (d$_6$-DMSO) 7.3 (m, 5H); 6.6 (m, 2H); 3.8 (s, 3H), 3.4 (s, 3H).

1-methyl-2-(2-methoxyphenyl)-5-aminobenzimidazole

Yield: 4.0 g; Rf (95/5/0.5 chloroform/methanol/aqueous ammonia): 0.25; Elem. anal. C$_{15}$H$_{15}$N$_3$O; theory C, 71.12; H, 5.97; N, 16.59. found C, 69.69; H, 6.53; N, 15.03. IR (KBr): 3230, 3200, 2935, 1625, 1460, 1245 cm$^{-1}$; $^1$H-NMR (d$_6$-DMSO) 7.5 (m, 2H); 7.1 (m, 3H); 6.7 (m, 2H); 3.8 (s, 3H); 3.4 (s, 3H).

43b) 1-methyl-2-(2-methoxyphenyl)-5-nitrobenzimidazole and 1-methyl-2-(2-methoxyphenyl)-6-nitrobenzimidazole Sodium hydride (22 g, 0.055 mol) and methyl iodide (3.15 ml, 0.050 mol) are added to 2-(2-methoxyphenyl)-5-nitrobenzimidazole (Example 37b, 12.38 g, 0.046 mol) in DMF (120 ml) at 0-5° C. The mixture is stirred at room temperature for 5 days. Water (300 ml) is added and the solid is filtered off and recrystallized from water, and then from 9/1 isopropyl ether/acetonitrile, to give a mixture of the two isomers in a ratio of about 65:35 respectively. Yield: 9.3 g (72%); Rf (9/1 toluene-methanol): 0.41 (isomer-6) and 0.36 (isomer 5); Elem. anal. C$_{15}$H$_{13}$N$_3$O$_3$; theory C, 63.59; H, 4.62; N, 14.83. found C, 63.34; H, 4.50; N, 14.70.

Example 44

Compound 44

N-[1-methyl-2-(2-methoxyphenyl)benzimidazol-6-yl]acetamidine

Prepared in a manner similar to that of Example 28 from 1-methyl-2-(2-methoxyphenyl)-6-aminobenzimidazole, Example 43a.

Yield: 87%; Elem. anal. C$_{17}$H$_{18}$N$_4$O; theory C, 69.37; H, 6.16; N, 19.03. found C, 67.95; H, 6.02; N, 18.38. IR (KBr): 3450, 3350, 1650, 1605, 1470, 1255 cm$^{-1}$; $^1$H-NMR (d$_6$-DMSO) 7.54 (dt, 1H); 7.49 (d, 1H); 7.45 (dd, 1H); 7.22 (d, 1H); 7.11 (t, 1H); 6.92 (broad s, 1H); 6.65 (d, 1H); 3.82 (s, 3H); 3.51 (s, 3H); 1.90 (s, 3H).

A number of physicochemical characteristics of compounds 1-44 are collated and given in Table 2.

TABLE 2

Physicochemical characteristics of representative compounds of formula (1)

| Compound | Empirical formula | Molecular weight | Melting point (° C.) | Rf (TLC) |
|---|---|---|---|---|
| 1 | $C_{15}H_{13}N_3S$ | 267.35 | 161.0-162.1 | 0.54[a] |
| 2 | $C_{15}H_{13}N_3 \cdot C_4H_4O_4$ | 383.41 | 202.5-203.2 | 0.54[a] |
| 3 | $C_{15}H_{12}ClN_3S$ | 301.79 | 212.2-213.5 | 0.49[a] |
| 4 | $C_{14}H_{19}N_3S$ | 261.39 | 112.6-114.7 | 0.53[a] |
| 5 | $C_{16}H_{15}N_3$ | 249.31 | 217.7-220.0 | 0.30[a] |
| 6 | $C_{17}H_{17}N_3$ | 263.34 | 184.6-185.8 | 0.40[a] |
| 7 | $C_{16}H_{15}N_3$ | 249.31 | 218.0-220.0 | 0.30[a] |
| 8 | $C_{17}H_{15}N_3$ | 261.33 | 143.0-144.4 | 0.52[a] |
| 9 | $C_{15}H_{13}N_3S$ | 267.35 | 177.0-178.0 | 0.48[a] |
| 10 | $C_{16}H_{15}N_3OS$ | 297.37 | 163.0-165.0 | 0.45[a] |
| 11 | $C_{16}H_{15}N_3S$ | 281.38 | 117.9-120.0 | 0.47[a] |
| 12 | $C_{17}H_{15}N_3S$ | 293.38 | 90.8-91.8 | 0.55[a] |
| 13 | $C_{16}H_{16}N_4O_3S_2 \cdot HCl$ | 412.91 | 244.0-248.0 | 0.40[a] |
| 14 | $C_{14}H_{12}N_4S$ | 268.34 | 187.2-188.9 | 0.29[a] |
| 15 | $C_{16}H_{15}N_3OS$ | 297.37 | 203.0-204.7 | 0.47[a] |
| 16 | $C_{17}H_{17}N_3O_2S$ | 327.40 | 156.4-158.3 | 0.50[a] |
| 17 | $C_{16}H_{15}N_3OS$ | 297.37 | 141.6-145.6 | 0.54[a] |
| 18 | $C_{16}H_{15}N_3S$ | 281.38 | 188.4-189.8 | 0.50[a] |
| 19 | $C_{15}H_{13}FN_4 \cdot 2HCl$ | 341.22 | 283.7-286.3 | 0.55[b] |
| 20 | $C_{15}H_{13}ClN_4$ | 284.75 | 153.6-156.0 | 0.61[a] |
| 21 | $C_{15}H_{14}N_4 \cdot HCl$ | 286.76 | 164.0-166.0 | 0.50[a] |
| 22 | $C_{14}H_{20}ClN_4 \cdot 2HCl$ | 317.22 | 276.9-278.3 | 0.50[a] |
| 23 | $C_{13}H_{13}N_5 \cdot 2HCl$ | 312.20 | 318.0-322.0 | 0.54[b] |
| 24 | $C_{13}H_{13}N_5 \cdot HBr$ | 320.19 | 197.0-199.0 | 0.54[b] |
| 25 | $C_{17}H_{16}N_4O_2 \cdot 2HCl$ | 381.26 | 284.0-288.0 | 0.20[a] |
| 26 | $C_{16}H_{14}N_4O_2$ | 294.31 | 271.5-274.3 | 0.59[d] |
| 27 | $C_{16}H_{14}N_4 \cdot 2HCl$ | 335.24 | 162.0-168.0 | 0.35[a] |
| 28 | $C_{16}H_{14}N_2O$ | 250.30 | 204.8-205.9 | 0.24[a] |
| 29 | $C_{15}H_{13}N_3O$ | 251.28 | 171.2-173.4° | 0.35[a] |
| 30 | $C_{15}H_{12}ClN_3O$ | 285.73 | 183.6-185.1 | 0.58[b] |
| 31 | $C_{16}H_{12}F_3N_3O$ | 319.29 | 157.9-159.2 | 0.64[a] |
| 32 | $C_{16}H_{12}F_3N_3O$ | 319.29 | 179.2-181.0 | 0.59[b] |
| 33 | $C_{15}H_{12}FN_3O$ | 269.27 | 157.9-159.2 | 0.64[c] |
| 34 | $C_{15}H_{12}Cl_2N_3O$ | 320.17 | 182.0-184.0 | 0.73[c] |
| 35 | $C_{15}H_{12}Cl_2N_4$ | 319.19 | 207.4-209.0 | 0.38[c] |
| 36 | $C_{16}H_{14}F_3N_4 \cdot HBr$ | 399.20 | 284.3-285.4 | 0.62[b] |
| 37 | $C_{16}H_{16}N_4O$ | 280.33 | 190.5-192.8 | 0.13[a] |
| 38 | $C_{15}H_{14}FN_4 \cdot HBr$ | 349.21 | 266.8-269.0 | 0.58[b] |
| 39 | $C_{16}H_{16}N_4$ | 264.33 | 154.0-158.0 | 0.40[c] |
| 40 | $C_{13}H_{12}N_4S$ | 256.33 | 166.7-169.1 | 0.31[a] |
| 41 | $C_{17}H_{15}N_3O$ | 277.32 | 137.4-138.9 | 0.63[b] |
| 42 | $C_{15}H_{13}N_3O$ | 251.28 | 176.3-177.8 | 0.44[a] |
| 43 | $C_{17}H_{18}N_4O \cdot 2HCl$ | 367.27 | 253.1-254.7 | 0.27[a] |
| 44 | $C_{17}H_{18}N_4O$ | 294.35 | 205.6-207.1 | 0.48[b] |

[a]Eluent: 85/25/1/2 $CHCl_3/MeOH/NH_3/H_2O$;
[b]Eluent: 5/2/2 n-butanol/AcOH/$H_2O$;
[c]Eluent: 73/25/2 $CHCl_3/MeOH/NH_3$;
[d]Eluent: 4/4/2 $CHCl_3/MeOH/NH_3$.

Other representative examples of compounds of Formula (I) are listed below:

N-[2-(3-methylphenyl)benzothiazol-5-yl]acetamidine;
N-[2-(4-methylphenyl)benzothiazol-5-yl]acetamidine;
N-[2-(2-fluorophenyl)benzothiazol-5-yl]acetamidine;
N-[2-(3-fluorophenyl)benzothiazol-5-yl]acetamidine;
N-[2-(4-fluorophenyl)benzothiazol-5-yl]acetamidine;
N-[2-(2-chlorophenyl)benzothiazol-5-yl]acetamidine;
N-[2-(3-chlorophenyl)benzothiazol-5-yl]acetamidine;
N-[2-(4-chlorophenyl)benzothiazol-5-yl]acetamidine;
N-[2-(3,4-dichlorophenyl)benzothiazol-5-yl]acetamidine;
N-[2-(4-trifluoromethylphenyl)benzothiazol-5-yl]acetamidine;
N-[2-(1-Methyl-1H-pyrrol-2-yl)benzothiazol-5-yl]acetamidine;
N-(2-Furan-2-ylbenzothiazol-5-yl)acetamidine;
N-(2-Furan-3-ylbenzothiazol-5-yl)acetamidine;
N-(2-phenylethylbenzothiazol-5-yl)acetamidine;
N-(2-Pentylbenzothiazol-5-yl)acetamidine;
N-[2-(4-fluorophenyl)benzothiazol-6-yl]acetamidine;
N-[2-(3-fluorophenyl)benzoxazol-5-yl]acetamidine;
N-[2-(4-fluorophenyl)benzoxazol-5-yl]acetamidine;
N-[2-(2,4-difluorophenyl)benzoxazol-5-yl]acetamidine;
N-[2-(3,4-difluorophenyl)benzoxazol-5-yl]acetamidine;
N-[2-(2-chlorophenyl)benzoxazol-5-yl]acetamidine;
N-[2-(3-chlorophenyl)benzoxazol-5-yl]acetamidine;
N-[2-(2-methoxyphenyl)benzoxazol-5-yl]acetamidine;
N-[2-(3-methoxyphenyl)benzoxazol-5-yl]acetamidine;
N-[2-(4-methoxyphenyl)benzoxazol-5-yl]acetamidine;
N-[2-(2,4-dimethoxyphenyl)benzoxazol-5-yl]acetamidine;
N-[2-(2-methylphenyl)benzoxazol-5-yl]acetamidine;
N-[2-(3-methylphenyl)benzoxazol-5-yl]acetamidine;
N-[2-(4-methylphenyl)benzoxazol-5-yl]acetamidine;
N-(2-benzylbenzoxazol-5-yl)acetamidine;
N-(2-styrylbenzoxazol-5-yl)acetamidine;
N-(2-phenylethylbenzoxazol-5-yl)acetamidine;
N-[2-(2-fluorophenyl)benzoxazol-6-yl]acetamidine;
N-[2-(3-fluorophenyl)benzoxazol-6-yl]acetamidine;
N-[2-(4-fluorophenyl)benzoxazol-6-yl]acetamidine;
N-[2-(2-chlorophenyl)benzoxazol-6-yl]acetamidine;
N-[2-(3-chlorophenyl)benzoxazol-6-yl]acetamidine;
N-[2-(4-chlorophenyl)benzoxazol-6-yl]acetamidine;
N-[2-(3,4-dichlorophenyl)benzoxazol-6-yl]acetamidine;
N-[2-(3-trifluoromethylphenyl)benzoxazol-6-yl]acetamidine;
N-[2-(4-trifluoromethylphenyl)benzoxazol-6-yl]acetamidine;
N-[2-(2-methoxyphenyl)benzoxazol-6-yl]acetamidine;
N-[2-(3-methoxyphenyl)benzoxazol-6-yl]acetamidine;
N-[2-(4-methoxyphenyl)benzoxazol-6-yl]acetamidine;
N-[2-(2,4-dimethoxyphenyl)benzoxazol-6-yl]acetamidine;
N-[2-(2-methylphenyl)benzoxazol-6-yl]acetamidine;
N-[2-(3-methylphenyl)benzoxazol-6-yl]acetamidine;
N-[2-(4-methylphenyl)benzoxazol-6-yl]acetamidine;
N-[2-(3-fluorophenyl)-3H-benzimidazol-5-yl]acetamidine;
N-[2-(2-chlorophenyl)-3H-benzimidazol-5-yl]acetamidine;
N-[2-(3-chlorophenyl)-3H-benzimidazol-5-yl]acetamidine;
N-[2-(4-trifluoromethylphenyl)-3H-benzimidazol-5-yl]acetamidine;
N-[2-(3-methoxyphenyl)-3H-benzimidazol-5-yl]acetamidine;
N-[2-(4-methoxyphenyl)-3H-benzimidazol-5-yl]acetamidine;
N-[2-(3,4-dimethoxyphenyl)-3H-benzimidazol-5-yl]acetamidine;
4-(5-acetimidoylamino-1H-benzimidazol-2-yl)benzamide;
N-[2-(pyrrol-3-yl)-3H-benzimidazol-5-yl]acetamidine;
N-[2-(furan-2-yl)-3H-benzimidazol-5-yl]acetamidine;
N-[2-(furan-3-yl)-3H-benzimidazol-5-yl]acetamidine;
N-[2-(thien-2-yl)-3H-benzimidazol-5-yl]acetamidine;
N-[2-(thien-3-yl)-3H-benzimidazol-5-yl]acetamidine;
N-[2-(2-methoxyphenyl)quinol-6-yl]acetamidine;
N-[2-(3-methoxyphenyl)quinol-6-yl]acetamidine;
N-[2-(4-methoxyphenyl)quinol-6-yl]acetamidine;
N-[2-(2-fluorophenyl)quinol-6-yl]acetamidine;
N-[2-(3-fluorophenyl)quinol-6-yl]acetamidine;
N-[2-(4-fluorophenyl)quinol-6-yl]acetamidine;
N-[2-(2-chlorophenyl)quinol-6-yl]acetamidine;
N-[2-(3-chlorophenyl)quinol-6-yl]acetamidine;
N-[2-(4-chlorophenyl)quinol-6-yl]acetamidine;
N-[2-(3,4-dichlorophenyl)quinol-6-yl]acetamidine;
N-[2-benzylquinol-6-yl]acetamidine;
N-[2-phenylethylquinol-6-yl]acetamidine;

N-(2-phenylquinol-7-yl)acetamidine;
N-[2-(2-methoxyphenyl)quinol-7-yl]acetamidine;
N-[2-(3-methoxyphenyl)quinol-7-yl]acetamidine;
N-[2-(4-methoxyphenyl)quinol-7-yl]acetamidine;
N-[2-(2-fluorophenyl)quinol-7-yl]acetamidine;
N-[2-(3-fluorophenyl)quinol-7-yl]acetamidine;
N-[2-(4-fluorophenyl)quinol-7-yl]acetamidine;
N-[2-(2-chlorophenyl)quinol-7-yl]acetamidine;
N-[2-(3-chlorophenyl)quinol-7-yl]acetamidine;
N-[2-(4-chlorophenyl)quinol-7-yl]acetamidine;
N-[2-(3,4-dichlorophenyl)quinol-7-yl]acetamidine;
N-(3-phenylisoquinol-6-yl)acetamidine;
N-[3-(4-fluorophenyl)isoquinol-6-yl]acetamidine;
N-[3-(4-chlorophenyl)isoquinol-6-yl]acetamidine;
N-[3-(4-trifluoromethylphenyl)isoquinol-6-yl]acetamidine;
N-[3-(3,4-dichlorophenyl)isoquinol-6-yl]acetamidine;
N-[2-(2-methoxyphenyl)quinazolin-6-yl]acetamidine;
N-[2-(3-methoxyphenyl)quinazolin-6-yl]acetamidine;
N-[2-(4-methoxyphenyl)quinazolin-6-yl]acetamidine;
N-[2-(2-fluorophenyl)quinazolin-6-yl]acetamidine;
N-[2-(3-fluorophenyl)quinazolin-6-yl]acetamidine;
N-[2-(4-fluorophenyl)quinazolin-6-yl]acetamidine;
N-[2-(2-chlorophenyl)quinazolin-6-yl]acetamidine;
N-[2-(3-chlorophenyl)quinazolin-6-yl]acetamidine;
N-[2-(4-chlorophenyl)quinazolin-6-yl]acetamidine;
N-[2-(4-trifluoromethylphenyl)quinazolin-6-yl]acetamidine;
N-[2-(3,4-dichlorophenyl)quinazolin-6-yl]acetamidine;
N-(2-benzylquinazolin-6-yl)acetamidine;
N-(2-styrylquinazolin-6-yl)acetamidine;
N-(2-phenylethylquinazolin-6-yl)acetamidine;
N-(2-phenylquinazolin-7-yl)acetamidine;
N-(2-phenyl-1H-indol-5-yl)acetamidine;
N-[2-(2-methoxyphenyl)-1H-indol-5-yl]acetamidine;
N-[2-(3-methoxyphenyl)-1H-indol-5-yl]acetamidine;
N-[2-(4-methoxyphenyl)-1H-indol-5-yl]acetamidine;
N-[2-(2-methylphenyl)-1H-indol-5-yl]acetamidine;
N-[2-(2-fluorophenyl)-1H-indol-5-yl]acetamidine;
N-[2-(3-fluorophenyl)-1H-indol-5-yl]acetamidine;
N-[2-(4-fluorophenyl)-1H-indol-5-yl]acetamidine;
N-[2-(2-chlorophenyl)-1H-indol-5-yl]acetamidine;
N-[2-(3-chlorophenyl)-1H-indol-5-yl]acetamidine;
N-[2-(4-chlorophenyl)-1H-indol-5-yl]acetamidine;
N-[2-(3-trifluoromethyl)-1H-indol-5-yl]acetamidine;
N-[2-(4-trifluoromethylphenyl)-1H-indol-5-yl]acetamidine;
N-[2-(3,4-dichlorophenyl)-1H-indol-5-yl]acetamidine;
N-(1-methyl-3-phenyl-1H-indol-5-yl)acetamidine;
N-(1-methyl-3-(4-chlorophenyl)-1H-indol-5-yl]acetamidine;
N-[2-(2-methoxyphenyl)benzofuran-5-yl]acetamidine;
N-[2-(3-methoxyphenyl)benzofuran-5-yl]acetamidine;
N-[2-(4-methoxyphenyl)benzofuran-5-yl]acetamidine;
N-[2-(2-methylphenyl)benzofuran-5-yl]acetamidine;
N-[2-(2-fluorophenyl)benzofuran-5-yl]acetamidine;
N-[2-(3-fluorophenyl)benzofuran-5-yl]acetamidine;
N-[2-(4-fluorophenyl)benzofuran-5-yl]acetamidine;
N-[2-(2-chlorophenyl)benzofuran-5-yl]acetamidine;
N-[2-(3-chlorophenyl)benzofuran-5-yl]acetamidine;
N-[2-(4-chlorophenyl)benzofuran-5-yl]acetamidine;
N-[2-(3-trifluoromethyl)benzofuran-5-yl]acetamidine;
N-[2-(4-trifluoromethylphenyl)benzofuran-5-yl]acetamidine;
N-[2-(3,4-dichlorophenyl)benzofuran-5-yl]acetamidine;
N-(2-benzylbenzofuran-5-yl)acetamidine;
N-(2-styrylbenzofuran-5-yl)acetamidine;
N-(2-phenylethylbenzofuran-5-yl)acetamidine;
N-(2-phenylbenzothiophen-5-yl)acetamidine;
N-[2-(2-methoxyphenyl)benzothiophen-5-yl]acetamidine;
N-[2-(3-methoxyphenyl)benzothiophen-5-yl]acetamidine;
N-[2-(4-methoxyphenyl)benzothiophen-5-yl]acetamidine;
N-[2-(2-fluorophenyl)benzothiophen-5-yl]acetamidine;
N-[2-(3-fluorophenyl)benzothiophen-5-yl]acetamidine;
N-[2-(4-fluorophenyl)benzothiophen-5-yl]acetamidine;
N-[2-(2-chlorophenyl)benzothiophen-5-yl]acetamidine;
N-[2-(3-chlorophenyl)benzothiophen-5-yl]acetamidine;
N-[2-(4-chlorophenyl)benzothiophen-5-yl]acetamidine;
N-[2-(4-trifluoromethylphenyl)benzothiophen-5-yl]acetamidine;
N-[2-(3,4-dichlorophenyl)benzothiophen-5-yl]acetamidine;
N-(2-benzylbenzothiophen-5-yl)acetamidine;
N-(2-styrylbenzothiophen-5-yl)acetamidine;
N-(2-phenylethylbenzothiophen-5-yl)acetamidine;
N-(2-phenylquinoxalin-6-yl)acetamidine;
N-[2-(4-fluorophenyl)quinoxalin-6-yl]acetamidine;
N-[2-(4-chlorophenyl)quinoxalin-6-yl]acetamidine;
N-[2-(3,4-dichlorophenyl)quinoxalin-6-yl]acetamidine;
N-(2-benzylquinoxalin-6-yl)acetamidine;
N-(2-styrylquinoxalin-6-yl)acetamidine;
N-(2-phenylethylquinoxalin-6-yl)acetamidine;
N-(2-phenylcinnolin-6-yl)acetamidine;
N-[2-(4-fluorophenyl)cinnolin-6-yl]acetamidine;
N-[2-(4-chlorophenyl)cinnolin-6-yl]acetamidine;
N-[2-(3,4-dichlorophenyl)cinnolin-6-yl]acetamidine;
N-(2-benzylcinnolin-6-yl)acetamidine;
N-(2-styrylcinnolin-6-yl)acetamidine;
N-(2-phenylethylcinnolin-6-yl)acetamidine;

Pharmacological Activity a) The inhibitory activity on the formation of NO measured as $NO_2^-$ (nitrite) and $PGE_2$ was studied in vitro on culture media of rabbit articular chondrocytes stimulated with the cytokine IL-1β (1 ng/ml) for 48 hours. For the preparation of the chondrocytes, the method described by Berenbaum et al. [FEBS Letters 340, 51-55 (1994)] was followed. Briefly, fragments of cartilage removed aseptically from the articular heads of rabbit shoulder, hip and knee were finely ground and digested at 37° C. in hyaluronidase, trypsin and collagenase solutions, giving, after filtration through sterile gauze and centrifugation at 600×g and suitable dilution with 10% DMEM-FCS 10%, a concentration per well of about $1×10^5$ cells. The cells were maintained under these conditions until confluent (about 15 days), the medium being replaced every 3 days. At this point, the test products dissolved in the medium were added to each sample and, after 20 minutes, 350 µl of IL-1β were added, to give a final concentration of 1 ng/ml. The stimulation lasted 48 hours at 37° C. (incubation in air/7% $CO_2$). A nitrite assay was subsequently performed on the cell supernatant, as described by Green et al. [Anal. Biochem. 126, 131-138 (1982)], and of $PGE_2$ by RIA assay. The results obtained are shown in Table 3, in which is given, for a number of the compounds that are the subject of the invention and that are already illustrated in Table 1, the $IC_{50}$, i.e. the concentration (micromolar) of antagonist capable of inhibiting the formation of nitrites and $PGE_2$ by 50% relative to the control group, i.e. relative to the cells stimulated with IL-1β but without addition of antagonists.

TABLE 3 in vitro Activity on rabbit articular chondrocytes stimulated with IL-1β

| Compound | Structure | Inhibition % IC$_{50}$ (x10$^{-6}$M) | |
|---|---|---|---|
| | | NO | PGE$_2$ |
| 1 | (structure: acetamidine-NH-benzothiazole-2-phenyl) | 6.5 | 2.4 |
| 3 | (structure: acetamidine-NH-benzothiazole-2-(4-Cl-phenyl)) | IN (tox 30) | 1.9 |
| 4 | (structure: acetamidine-NH-benzothiazole-2-n-Pent) | 6.9 | 6.6 |
| 5 | (structure: acetamidine-NH-indole-2-phenyl) | 3.4 | 1.2 |
| 6 | (structure: acetamidine-NH-(N-Me-indole)-2-phenyl) | IN (tox 30) | IN (tox 30) |
| 8 | (structure: acetamidine-NH-quinoline-2-phenyl) | 47.9 | 2.3 |
| 9 | (structure: 5-acetamidine-NH-benzothiazole-2-phenyl) | 18.0 | 4.2 |
| 10 | (structure: acetamidine-NH-benzothiazole-2-(2-MeO-phenyl)) | IN (tox 100) | 5.9 |
| 11 | (structure: acetamidine-NH-benzothiazole-2-benzyl) | 15.0 | 7.4 |

TABLE 3-continued in vitro Activity on rabbit articular chondrocytes stimulated with IL-1β

| Compound | Structure | Inhibition % IC$_{50}$ (x10$^{-6}$M) | |
|---|---|---|---|
| | | NO | PGE$_2$ |
| 12 | | 88.9 | 1.3 |
| 13 | | IN | 16.2 |
| 14 | | IN | 42.5 |
| 15 | | IN (tox 30) | 7.4 |
| 16 | | IN (tox 30) | IN |
| 17 | | IN (tox 30) | 1.3 |
| 18 | | 6.2 | 1.2 |
| 19 | | 78 | 0.7 |
| 20 | | 22.8 | 0.4 |
| 21 | | 84.5 | 0.8 |

TABLE 3-continued in vitro Activity on rabbit articular chondrocytes stimulated with IL-1β

| Compound | Structure | Inhibition % IC$_{50}$ (×10$^{-6}$M) | |
|---|---|---|---|
| | | NO | PGE$_2$ |
| 22 | [acetimidamide-benzimidazole-2-n-pentyl] | 123 | 31.5 |
| 23 | [acetimidamide-benzimidazole-2-pyrrole] | 250 | 2.0 |
| 25 | [acetimidamide-benzimidazole-2-(4-COOMe-phenyl)] | 174 | IN |
| 26 | [acetimidamide-benzimidazole-2-(4-COOH-phenyl)] | IN | IN |
| 27 | [acetimidamide-2-phenyl-quinazoline] | 67.5 | 9.0 |
| 28 | [acetimidamide-2-phenyl-benzofuran] | 7.8 | 0.5 |
| 29 | [acetimidamide-2-phenyl-benzoxazole] | 28.6 | 3.2 |
| 30 | [acetimidamide-2-(4-Cl-phenyl)-benzoxazole] | IN (tox 30) | 0.3 |
| 31 | [acetimidamide-2-(3-CF$_3$-phenyl)-benzoxazole] | 11.2 | 2.9 |
| 32 | [acetimidamide-2-(4-CF$_3$-phenyl)-benzoxazole] | 8.1 | 0.6 |

TABLE 3-continued
in vitro Activity on rabbit articular chondrocytes stimulated with IL-1β
| Compound | Structure | Inhibition % IC$_{50}$ (x10$^{-6}$M) | |
| --- | --- | --- | --- |
| | | NO | PGE$_2$ |
| 33 | 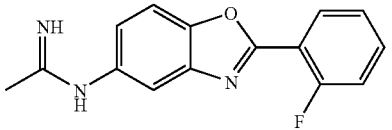 | 47.0 | 13.8 |
| 34 | 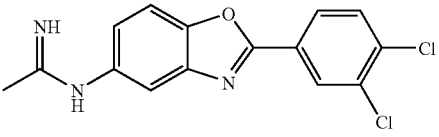 | 4.3 | 0.4 |
| 35 | 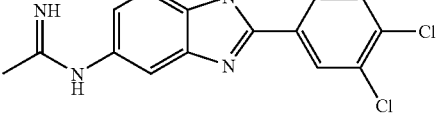 | IN | 0.4 |
| 36 | 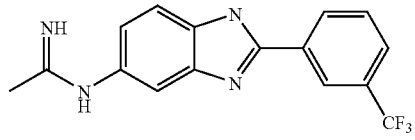 | IN | IN |
| 37 | 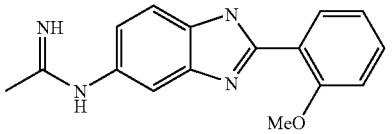 | 32.1 | 2.8 |
| 38 | 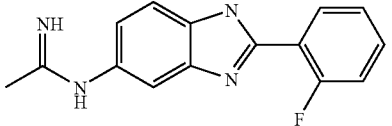 | IN | IN |
| 39 | 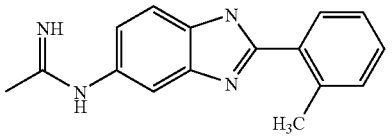 | 199 | 9.9 |
| 40 | 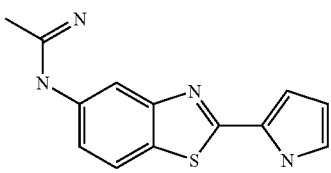 | IN | 8.4 |
| 41 | 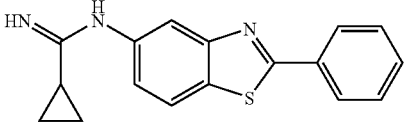 | IN | 4.0 |

TABLE 3-continued in vitro Activity on rabbit articular chondrocytes stimulated with IL-1β

| Compound | Structure | Inhibition % $IC_{50}$ (x$10^{-6}$M) | |
|---|---|---|---|
| | | NO | $PGE_2$ |
| 42 | | 42.9 | 5.1 |
| L-NAME | — | 71.0 | IN |
| CELECOXIB | — | IN | 0.02 |

Note: IN = <25% inhibitory activity at 30 × $10^{-6}$M
Tox = cellular toxicity

From the data given in Table 3, it may be deduced that some of the test compounds that are subjects of the invention show a powerful inhibitory effect, at the micromolar level, on the production of NO.

The most active compounds are the benzothiazole derivatives, compounds 1, 4 and 18, the indole derivative 5, the benzofuran derivative 28 and the benzoxazole derivative 34, all having an activity of between 3 and 8 micromolar.

Generally, a substitution with halogen on the phenyl group increases the activity: see for example compound 34 (3,4-dichloro derivative relative to the unsubstituted analogous compound, compound 29), thus there is often a corresponding increase in the cytotoxicity that precludes the objective evaluation of the activity of these compounds. It should also be noted that the NO-synthase inhibitor reference compound, L-NAME, shows activity that is about 10-fold less powerful than that of the best compounds that are the subject of the invention on this experimental model ($IC_{50}$ 71 micromolar).

Some of the compounds that are the subject of the invention also inhibit the IL-1β-induced production of prostaglandins ($PGE_2$) at sub-micromolar concentrations. Thus, the benzimidazole compounds 19, 20, 21 and 35, the benzoxazole compounds 30 and 34 and the benzofuran compound 28 inhibit the formation of $PGE_2$ at concentrations ($IC_{50}$) of between 0.3 and 0.8 micromolar.

The inhibitory activity on the production of $PGE_2$ by many of the compounds that are the subject of the invention is probably at least partly due to their capacity to inhibit the production of NO.

In point of fact, it has been described that NO potentiates the cytokine-induced production of $PGE_2$ in a variety of cell systems [see for example Watkins et al.; Br. J. Pharmacol. 121 (1997), 1482-1488].

This effect appears to be due to the amplification of the expression of COX-2 (Tetsuka et al.; J. Clin. Invest. 97 (1996), 2051-2056). For the compounds that are the subject of the invention that show little activity as NO-production inhibitors while inhibiting the production of $PGE_2$ at the sub-micromolar level, for instance the benzimidazole derivatives 19, 20, 21 and 35 or the benzothiazole derivatives 12, the inhibitory activity on $PGE_2$ production is probably associated with a direct action on the inducible cyclooxygenase enzyme.

The selective antagonist of the inducible cyclooxygenase (COX-2), Celecoxib, chosen as comparative compound, was found to be about ten times more powerful in inhibiting the production of $PGE_2$ than the most active compounds that are the subject of the invention, whereas it was entirely inactive as regards inhibiting the production of NO.

Some of the compounds that are the subject of the invention also demonstrated inhibition of the expression (mRNA) of IL-6 in isolated human chondrosarcoma cells (SW 1353) stimulated with IL-1β. In practice, the RNA extracted from the cells was back-transcribed to c-DNA by means of a thermocycler (BioRad—"iCycler") and subsequently amplified via the Real Time PCR technique using a probe and a primer specific for IL-6, from the company Applied Biosystem, and the thermocycler 7000 Sequence Detection System (Applied Biosystem).

Using this technique, for example, compounds 5, 8, 9, 18, 27, 28 and 29 were found to inhibit the expression of IL-6 in SW 1353 cells stimulated for 6 hours with IL-Lβ with an $IC_{50}$ of between 1.5 and 6 micromolar. The capacity of IL-6 to inhibit the expression of messenger RNA may be considered as large, since the increase in the expression of this cytokine is associated with the physiopathology of various human diseases, for instance Crohn's disease, as described previously.

Some of the compounds that are the subject of the invention, which showed the strongest activity in the in vitro tests described hereinabove, were evaluated "in vivo" in rats on experimental models of inflammation and hyperalgesia induced by zymosan. This is a phlogogenic agent, consisting of a protein-glycoside complex, extracted from the cell walls of raw yeast, which is capable of inducing rapid degranulation of neutrophils, an increase in the production of TNF-α, interleukin-1 (IL-1), IL-6 and stimulation of NO generation by monocytes and macrophages (zymosaN:Merck Index XIII ed. No. 10250, p. 1818).

The experiments consisted of sub-plantar intradermal injection into the animal of 4 mg of zymosan suspended in 100 μl of sterile physiological solution, while the test compounds were administered orally 30 minutes before injection of the phlogogenic agent.

Measurement of the inflammation of the injected paw and of the consequent hyperalgesic effects was performed 2, 4 and 6 hours after the administration of zymosan. The oedema was evaluated as the increase in volume of the injected paw within the period 0-6 hours, relative to the initial value of the volume of the paw, i.e. before the injection of zymosan (basal value).

The measurements of the variation of the volume of the paw were recorded using a hydroplethysmometer (Mod. 7150, Basile, Italy), which consists of two plastic cuvettes containing a surfactant liquid, the larger one being used for immersion of the paw, connected to the smaller one which contains a transducer capable of recording small displacements of volume of the liquid used for the measurement. The paw is immersed in the cuvettes up to the tibiotarsal joint. The volume of liquid displaced by the paw indicates the magnitude of the inflammation.

For each test compound, at least three doses were used (generally 10, 20 and 40 mg/kg) with at least five animals per group×dose, so as to be able to calculate an $ED_{30}$, i.e. the dose in mg/kg capable of reducing by 30% the zymosan-induced volume increase, relative to the group of control animals, i.e. animals injected only with the phlogogenic agent and treated orally with distilled water.

The hyperalgesia induced by the intradermal administration of zymosan was evaluated on these animals and at the same times described previously for the evaluation of the oedema, using the Randall-Selitto method [Arch. Int. Pharmacodyn. 111, 409 (1957)].

In practice, an analgesimeter was used (Basile, Italy), which consists in applying to the inflamed paw a weight in the form of a rounded-tipped cone, on which the applied force is gradually increased. When the animal makes a noise following the pain stimulus, the operator blocks the punch and records the force, expressed in grams, which was applied to the paw (the cut-off value is 500 grams). The difference in the meal chanical pain threshold between the basal value (generally about 230-250 grams) and that recorded at the indicated times after injection of the phlogogenic agent, generally 130-140 g for the control animals 6 hours after injection of the phlogogenic agent, is defined as mechanical hyperalgesia. In this case also, an $ED_{30}$ was calculated, i.e. the dose in mg/kg capable of increasing the pain threshold by 30% (meal chanical hyperalgesia) in the animals treated with the test compounds relative to the group of control animals.

The results thus obtained are given in Table 4, which presents the $ED_{30}$ values for the anti-inflammatory and anti-hyperalgesic activity for a number of compounds that are the subject of the invention, compared with those obtained with Celecoxib and L-NAME.

TABLE 4

Anti-inflammatory and analgesic activity (measured in the range 0-6 hours) in rat paw injected with Zymosan.
($ED_{30}$ mg/kg os)

| Compounds | Anti-inflammatory activity (oedema) | Analgesic activity (mechanical anti-hyperalgesia) | Mean (Oedema + Analgesia) |
|---|---|---|---|
| 1 | 12.6 | 6.7 | 9.7 |
| 5 | 39.4 | 19.3 | 29.4 |
| 8 | 19.8 | 11.8 | 15.8 |
| 9 | 33.9 | 31.3 | 32.6 |
| 27 | 24.6 | 13.0 | 18.8 |
| 28 | 20.8 | 24.4 | 22.6 |
| Celecoxib | 79.4 | 69.2 | 74.3 |
| L-NAME | IN | IN | IN |

Note:
the compound L-NAME was entirely inactive up to the maximum dose administered (50 mg/kg).

As may be deduced from the data given above in Table 4, many of the compounds that are the subject of the invention, for instance the benzothiazole derivatives, compounds 1 and 9, the indole derivative, compound 5, the quinoline derivative, compound 8, the quinazoline derivative, compound 27, and the benzofuran derivative, compound 28, show powerful anti-inflammatory and anti-hyperalgesic action even when admin-istered orally, indicating that they therefore have good bioavailability. On average, using the compounds illustrated, and considering overall both the anti-oedema-generating activity and the analgesic activity, an activity about 2 to 7 times higher than that of the selective COX-2 antagonist Celecoxib is obtained.

The NO-synthase antagonist L-NAME was inactive up to the maximum dose tested (50 mg/kg) since, besides having an intrinsic activity that is generally lower than that of the compounds that are the subject of the invention, it may probably also be poorly absorbed via the oral route.

In conclusion, by means of the combined action of inhibition of the production of NO and, indirectly, that of the prostaglandin $PGE_2$, along with the action of inhibiting the expression of pro-inflammatory cytokines such as IL-6, many of the compounds that are the subject of the invention show in vivo an anti-inflammatory and analgesic effect that is greater than both that of Celecoxib, i.e. a powerful and selective antagonist of inducible cyclooxygenase (COX-2), and than that of L-NAME, an NO-synthase antagonist.

What is claimed is:
1. A compound of formula (I):

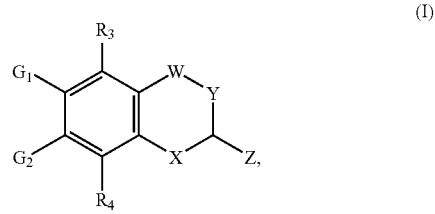

(I)

wherein:
one of $G_1$ or $G_2$ is an amidine substituent of formula Q, and the other of $G_1$ or $G_2$ is independently selected from hydrogen, halogen, hydroxyl, $C_1$-$C_4$ alkoxy and $C_1$-$C_4$ alkyl;
the amidine substituent of formula Q is represented by the structure given below, in which R is $C_1$-$C_4$ alkyl or cycloalkyl;

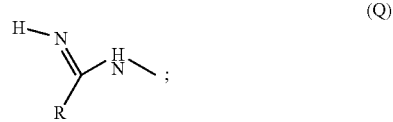

(Q)

W independently represents a bond,
Y is =N—;
X is —S—;
$R_1$ and $R_2$ are independently selected from hydrogen, $C_1$-$C_4$ alkyl, $C_2$-$C_4$ alkenyl and $C_1$-$C_4$ alkoxy;
$R_3$ and $R_4$ are independently selected from hydrogen, halogen, hydroxyl, $C_1$-$C_4$ alkoxy, $C_1$-$C_4$ alkyl and $C_2$-$C_4$ alkenyl;
z is an aryl group, heteroaryl group, a linear or branched $C_1$-$C_6$ alkyl or $C_2$-$C_6$ alkenyl chain, $C_1$-$C_4$ alkylene-aryl group, $C_1$-$C_4$ alkylene-heteroaryl group, wherein, the aryl group is a phenyl which is unsubstituted or substituted with one or more substituents independently selected from halogen, trifluoromethyl, hydroxyl, nitro, cyano, carboxyl, carboxamido, carbonyl, thio, methylthio, methanesulfonyl, methanesulfinyl, sulfonamido, trifluoromethoxy, $C_1$-$C_6$ alkoxy and $C_1$-$C_6$ alkyl, and the heteroaryl group is a 5- or 6-atom heterocyclic aromatic ring containing one or more hetero atoms, which is unsubstituted or substituted with one or more substituents independently selected from halogen, trifluoromethyl, hydroxyl, nitro, cyano, carboxyl, carbonyl, thio, methylthio, methanesulfonyl, methanesulfinyl, trifluoromethoxy, $C_1$-$C_6$ alkoxy and $C_1$-$C_6$ alkyl; the $C_1$-$C_4$ alkylene-aryl group is a linear or branched, saturated or unsaturated alkylene chain substituted with an aryl group provided that when the $C_1$-$C_4$ alkylene chain is unsaturated, it has only one substituted or an unsubstituted double bond; substituents for the aryl group are independently selected from the groups defined above as substituents for the aryl group; the $C_1$-$C_4$ alkylene-heteroaryl group is a linear or branched, saturated or unsaturated alkylene chain substituted with a substituted or an unsubstituted heteroaryl group; provided that when the $C_1$-$C_4$ alkylene chain is unsaturated, it has only one substituted or unsubstituted double bond;

and or pharmaceutically acceptable salts thereof.

2. The compound according to claim 1 wherein:

$G_1$ and $G_2$ are independently selected from H (hydrogen) and the amidine substituent of formula Q wherein R is a methyl, provided that one of the two groups $G_1$ and $G_2$ must be hydrogen;

$R_3$ and $R_4$ are both hydrogen;

z is an aryl or heteroaryl group, a linear or branched $C_3$-$C_6$ alkyl or alkenyl chain, a $C_1$-$C_4$ alkylene-aryl or alkenylaryl group, or a $C_1$-$C_4$ alkylene-heteroaryl group.

3. The compound according to claim 1, wherein the pharmaceutically acceptable salts are selected from the group consisting of hydrochloride, hydrobromide, sulfate, hydrogen sulfate, methanesulfonate, maleate, citrate, fumarate and succinate.

4. A pharmaceutical preparation of a composition comprising, mixing as active substances, at least one compound according to claim 1, or a pharmaceutically acceptable salt thereof, and optionally a pharmaceutically acceptable vehicle.

5. A method for the therapeutic treatment of acute or chronic pain of articular or neuropathic origin, comprising administering the pharmaceutical preparation according to claim 4.

6. A pharmaceutical preparation of a composition comprising, mixing as active substances, at least one compound of formula (I):

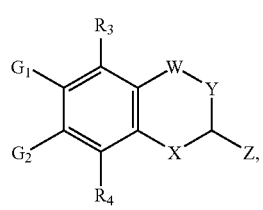

(I)

wherein:

one of $G_1$ or $G_2$ is an amidine substituent of formula Q, and the other of $G_1$ or $G_2$ is independently selected from hydrogen, halogen, hydroxyl, $C_1$-$C_4$ alkoxy and $C_1$-$C_4$ alkyl;

the amidine substituent of formula Q is represented by the structure given below, in which R is $C_1$-$C_4$ alkyl or cycloalkyl;

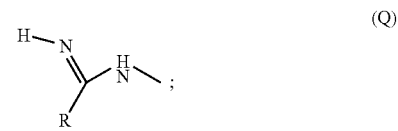

(Q)

W independenfly represents a bond;

Y is =N—;

X is —S—;

$R_1$ and $R_2$ are independently selected from hydrogen, $C_1$-$C_4$ alkyl, $C_2$-$C_4$ alkenyl and $C_1$-$C_4$ alkoxy;

$R_3$ and $R_4$ are independently selected from hydrogen, halogen, hydroxyl, $C_1$-$C_4$ alkoxy, $C_1$-$C_4$ alkyl and $C_2$-$C_4$ alkenyl;

z is an aryl group, heteroaryl group, a linear or branched $C_1$-$C_6$ alkyl or $C_2$-$C_6$ alkenyl chain, $C_1$-$C_4$ alkylene-aryl group, $C_1$-$C_4$ alkylene-heteroaryl group, wherein, the aryl group is a phenyl which is unsubstituted or substituted with one or more substituents independently selected from halogen, trifluoromethyl, hydroxyl, nitro, cyano, carboxyl, carboxamido, carbonyl, thio, methylthio, methanesulfonyl, methanesulfinyl, sulfonamido, trifluoromethoxy, $C_1$-$C_6$ alkoxy and $C_1$-$C_6$ alkyl, and the heteroaryl group is a 5- or 6-atom heterocyclic aromatic ring containing one or more hetero atoms, which is unsubstituted or substituted with one or more substituents independently selected from halogen, trifluoromethyl, hydroxyl, nitro, cyano, carboxyl, carbonyl, thio, methylthio, methanesulfonyl, methanesulfinyl, trifluoromethoxy, $C_1$-$C_6$ alkoxy and $C_1$-$C_6$ alkyl; the $C_1$-$C_4$ alkylene-aryl group is a linear or branched, saturated or unsaturated alkylene chain substituted with an aryl group provided that when the $C_1$-$C_4$ alkylene chain is unsaturated, it has only one substituted or an unsubstituted double bond; substituents for the aryl group are independently selected from the groups defined above as substituents for the aryl group; the $C_1$-$C_4$ alkylene-heteroaryl group is a linear or branched, saturated or unsaturated alkylene chain substituted with a substituted or an unsubstituted heteroaryl group; provided that when the $C_1$-$C_4$ alkylene chain is unsaturated, it has only one substituted or unsubstituted double bond;

and or a pharmaceutically acceptable salt thereof, and optionally a pharmaceutically acceptable vehicle comprising pharmaceutically acceptable inactive ingredients chosen from the group consisting of vehicles, binders, flavourings, sweeteners, disintegrants, preserving agents, humectants and mixtures thereof, or ingredients to facilitate rectal, transdermal or transmucosal absorption or that allow controlled release of the active substance over time, and also ingredients suitable for parenteral use, selected from intravenous, intramuscular, subcutaneous, intradermal and intra-articular administration, wherein salified compounds of formula (I)and or pharmaceutical acceptable salts thereof are used.

7. Process for preparing a compound of formula (I), according to claim 1, comprising: reacting a compound of formula (II)

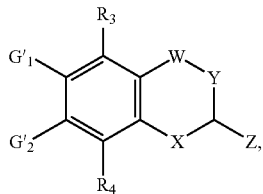

wherein:
W is a bond,
Y is =N—;
X is —S—;
z is an aryl, heteroaryl, linear or branched $C_1$-$C_6$ alkyl, alkenyl chain, $C_1$-$C_4$ alkylene-aryl group, $C_1$-$C_4$ alkylene-heteroaryl group, wherein, the aryl group is a phenyl which is unsubstituted or substituted with one or more substituents independently selected from halogen, trifluoromethyl, hydroxyl, nitro, cyano, carboxyl, carboxamido, carbonyl, thio, methylthio, methanesulfonyl, methanesulfinyl, sulfonamido, trifluoromethoxy, $C_1$-$C_6$ alkoxy and $C_1$-$C_6$ alkyl, and the heteroaryl group is a 5- or 6-atom heterocyclic aromatic ring containing one or more hetero atoms, which is unsubstituted or substituted with one or more substituents independently selected from halogen, trifluoromethyl, hydroxyl, nitro, cyano, carboxyl, carbonyl, thio, methylthio, methanesulfonyl, methanesulfinyl, trifluoromethoxy, $C_1$-$C_6$ alkoxy and $C_1$-$C_6$ alkyl; the $C_1$-$C_4$ alkylene-aryl group is a linear or branched, saturated or unsaturated alkylene chain substituted with an aryl group, provided that when the $C_1$-$C_4$ alkylene chain is unsaturated, it has only one substituted or an unsubstituted double bond; substituents for the aryl group are independently selected from the groups defined above as substituents for the aryl group; the $C_1$-$C_4$ alkylene-heteroaryl group is a linear or branched, saturated or unsaturated $C_1$-$C_4$ alkylene chain substituted with a substituted or an unsubstituted heteroaryl group; provided that when the $C_1$-$C_4$ alkylene chain is unsaturated, it has only one substituted or unsubstituted double bond;
$R_1$ and $R_2$ are independently selected from hydrogen, $C_1$-$C_4$ alkyl, $C_2$-$C_4$ alkenyl and $C_1$-$C_4$ alkoxy;
$R_3$ and $R_4$ are independently selected from hydrogen, halogen, hydroxyl, $C_1$-$C_4$ alkoxy, $C_1$-$C_4$ alkyl and C2-$C_4$ alkenyl;
$G'_1$ and $G'_2$ are independently selected from: hydrogen, halogen, hydroxyl, $C_1$-$C_4$ alkoxy, $C_1$-$C_4$ alkyl, and —$NH_2$—, provided that, for each compound of formula (II), one of the two substituents $G'_1$ or $G'_2$ is —$NH_2$—,
with a compound of formula (III)

wherein:
L is an alkoxy group, an alkylthio group or an arylthio group,
in a suitable solvent at temperatures of between 0° C. and 50° C.; and
optionally, converting a compound of formula (II) into a compound of formula (I) by the removal of any protecting groups;
recovering the compounds of formula (I) from the reaction mass;
purifying the compounds; and
isolating the compounds in unmodified form or in the form of pharmaceutically acceptable salts.

8. A method for the therapeutic treatment of acute or chronic pain of articular or neuropathic origin, comprising administering a pharmaceutical preparation comprising, mixing as active substances, at least one compound according to claim 1, or a pharmaceutically acceptable salt thereof, and optionally a pharmaceutically acceptable vehicle, wherein the articular origin is rheumatoid arthritis or osteoarthritis.

* * * * *